US008992538B2

United States Patent
Keefer

(10) Patent No.: US 8,992,538 B2
(45) Date of Patent: Mar. 31, 2015

(54) CUSTOMIZED PATIENT-SPECIFIC ACETABULAR ORTHOPAEDIC SURGICAL INSTRUMENT AND METHOD OF USE AND FABRICATION

(75) Inventor: Ryan Keefer, Fort Wayne, IN (US)

(73) Assignee: DePuy Synthes Products, Inc., Raynham, MA (US)

( * ) Notice: Subject to any disclaimer, the term of this patent is extended or adjusted under 35 U.S.C. 154(b) by 1152 days.

(21) Appl. No.: 12/543,156

(22) Filed: Aug. 18, 2009

(65) Prior Publication Data

US 2010/0082035 A1 Apr. 1, 2010

Related U.S. Application Data

(60) Provisional application No. 61/101,524, filed on Sep. 30, 2008.

(51) Int. Cl.
*A61F 5/00* (2006.01)
*A61B 17/17* (2006.01)
*A61B 17/56* (2006.01)
*A61B 19/00* (2006.01)

(52) U.S. Cl.
CPC ....... *A61B 17/1746* (2013.01); *A61B 2017/568* (2013.01); *A61B 2019/508* (2013.01)
USPC .................................. 606/87; 606/81; 606/91

(58) Field of Classification Search
USPC ............. 606/54–59, 79–81, 86 R, 87–91, 96; 623/22.11–22.46
See application file for complete search history.

(56) References Cited

U.S. PATENT DOCUMENTS

| | | | |
|---|---|---|---|
| 3,698,017 A | 10/1972 | Scales et al. |
| 3,840,904 A | 10/1974 | Tronzo |
| 3,903,549 A | 9/1975 | Deyerle et al. |
| 4,475,549 A | 10/1984 | Oh et al. |
| 4,632,111 A | 12/1986 | Roche et al. |
| 4,711,233 A | 12/1987 | Brown |
| 4,715,860 A | 12/1987 | Amstutz et al. |
| 4,800,874 A | 1/1989 | David et al. |
| 5,007,936 A | 4/1991 | Woolson et al. |

(Continued)

FOREIGN PATENT DOCUMENTS

| CA | 2501041 A1 | 4/2004 |
|---|---|---|
| CA | 2505371 A1 | 5/2004 |

(Continued)

OTHER PUBLICATIONS

Radermacher et al., "Computer Assisted Orthopaedic Surgery with Image Based Individual Templates", Clin Orthopaedics and Related Research 354, 28-38, 1998, 11 pages.

(Continued)

*Primary Examiner* — Matthew Lawson
(74) *Attorney, Agent, or Firm* — Barnes & Thornburg LLP

(57) ABSTRACT

A customized patient-specific orthopaedic instrument for facilitating implantation of an acetabular cup prosthesis in a coxal bone of a patient includes a customized patient-specific acetabular reaming guide. The customized patient-specific acetabular reaming guide includes a longitudinal passageway for an acetabular reamer and a plurality of arms with attached feet. Each foot of the reaming guide is positioned relative to the body based on the contours of the coxal bone of the patient and a predetermined degree of version and inclination angles of the acetabular cup prosthesis when implanted in the patient's coxal bone.

10 Claims, 21 Drawing Sheets

(56) References Cited

U.S. PATENT DOCUMENTS

| | | |
|---|---|---|
| 5,098,437 A | 3/1992 | Kashuba et al. |
| 5,108,401 A | 4/1992 | Insall et al. |
| 5,133,660 A | 7/1992 | Fenick |
| 5,171,243 A | 12/1992 | Kashuba et al. |
| 5,320,529 A | 6/1994 | Pompa |
| 5,320,625 A | 6/1994 | Bertin et al. |
| 5,658,294 A | 8/1997 | Sederholm et al. |
| 5,768,134 A | 6/1998 | Swaelens et al. |
| 5,817,097 A | 10/1998 | Howard et al. |
| 5,824,085 A | 10/1998 | Sahay et al. |
| 5,942,370 A | 8/1999 | Neckers et al. |
| 5,976,149 A | 11/1999 | Masini et al. |
| 6,161,080 A | 12/2000 | Aouni-Ateshian et al. |
| 6,228,121 B1 | 5/2001 | Khalili |
| 6,264,698 B1 | 7/2001 | Lawes et al. |
| 6,273,891 B1 | 8/2001 | Masini |
| 6,327,491 B1* | 12/2001 | Franklin et al. ............... 600/429 |
| 6,344,043 B1 | 2/2002 | Pappas |
| 6,395,005 B1 | 5/2002 | Lovell |
| 6,427,698 B1 | 8/2002 | Yoon |
| 6,463,351 B1 | 10/2002 | Clynch |
| 6,944,518 B2 | 9/2005 | Roose |
| 6,953,480 B2 | 10/2005 | Mears et al. |
| 6,991,655 B2 | 1/2006 | Iversen |
| 7,534,263 B2 | 5/2009 | Burdulis, Jr. et al. |
| 7,559,931 B2 | 7/2009 | Stone |
| 7,618,451 B2 | 11/2009 | Berez et al. |
| 7,634,119 B2 | 12/2009 | Tsougarakis et al. |
| 7,651,501 B2 | 1/2010 | Penenberg et al. |
| 7,717,956 B2 | 5/2010 | Lang |
| 7,796,791 B2 | 9/2010 | Tsougarakis et al. |
| 7,824,181 B2 | 11/2010 | Sers |
| 7,981,158 B2 | 7/2011 | Fitz et al. |
| 8,133,234 B2 | 3/2012 | Meridew et al. |
| 8,175,683 B2 | 5/2012 | Roose |
| 8,808,302 B2 | 8/2014 | Roose et al. |
| 2002/0007294 A1 | 1/2002 | Bradbury et al. |
| 2004/0204760 A1 | 10/2004 | Fitz et al. |
| 2004/0236424 A1 | 11/2004 | Berez et al. |
| 2005/0107799 A1 | 5/2005 | Graf et al. |
| 2005/0148843 A1 | 7/2005 | Roose |
| 2005/0234461 A1 | 10/2005 | Burdulis et al. |
| 2005/0267584 A1 | 12/2005 | Burdulis et al. |
| 2006/0129160 A1 | 6/2006 | Liu et al. |
| 2007/0106305 A1* | 5/2007 | Kao et al. ............... 606/130 |
| 2007/0198022 A1* | 8/2007 | Lang et al. ............... 606/88 |
| 2007/0276400 A1 | 11/2007 | Moore et al. |
| 2008/0114370 A1 | 5/2008 | Schoenefeld |
| 2008/0147072 A1 | 6/2008 | Park et al. |
| 2008/0161815 A1 | 7/2008 | Schoenefeld et al. |
| 2008/0234665 A1* | 9/2008 | Godara et al. ............... 606/1 |
| 2008/0234685 A1 | 9/2008 | Gjerde |
| 2008/0243127 A1 | 10/2008 | Lang et al. |
| 2008/0275452 A1 | 11/2008 | Lang et al. |
| 2008/0281328 A1 | 11/2008 | Lang et al. |
| 2008/0281329 A1 | 11/2008 | Fitz et al. |
| 2008/0281426 A1 | 11/2008 | Fitz et al. |
| 2008/0287954 A1 | 11/2008 | Kunz et al. |
| 2008/0306558 A1 | 12/2008 | Hakki |
| 2009/0088674 A1 | 4/2009 | Caillouette et al. |
| 2009/0131941 A1 | 5/2009 | Park et al. |
| 2009/0138020 A1 | 5/2009 | Park et al. |
| 2009/0149977 A1 | 6/2009 | Schendel |
| 2009/0163922 A1 | 6/2009 | Meridew et al. |
| 2009/0222014 A1 | 9/2009 | Bojarski et al. |
| 2009/0270868 A1 | 10/2009 | Park et al. |
| 2009/0307893 A1 | 12/2009 | Burdulis, Jr. et al. |
| 2010/0016984 A1 | 1/2010 | Trabish |
| 2010/0023015 A1 | 1/2010 | Park |
| 2010/0042105 A1 | 2/2010 | Park et al. |
| 2010/0082035 A1 | 4/2010 | Keefer |
| 2010/0087829 A1 | 4/2010 | Metzger et al. |
| 2010/0152782 A1 | 6/2010 | Stone et al. |
| 2010/0160917 A1 | 6/2010 | Fitz et al. |
| 2010/0168754 A1 | 7/2010 | Fitz et al. |
| 2010/0191244 A1 | 7/2010 | White et al. |
| 2010/0212138 A1 | 8/2010 | Carroll et al. |
| 2010/0217338 A1 | 8/2010 | Carroll et al. |
| 2010/0274253 A1 | 10/2010 | Ure |
| 2011/0015639 A1 | 1/2011 | Metzger et al. |

FOREIGN PATENT DOCUMENTS

| | | |
|---|---|---|
| CA | 2505419 A1 | 6/2004 |
| CA | 2506849 A1 | 6/2004 |
| CA | 2546958 A1 | 6/2005 |
| CA | 2546965 A1 | 6/2005 |
| CA | 2588907 A1 | 6/2006 |
| CA | 2590534 A1 | 6/2006 |
| CN | 1728976 A | 2/2006 |
| CN | 1729483 A | 2/2006 |
| CN | 1729484 A | 2/2006 |
| CN | 1913844 A | 2/2007 |
| CN | 101111197 A | 1/2008 |
| DE | 2830566 A1 | 1/1980 |
| DE | 4219939 A1 | 12/1993 |
| EP | 0645984 A1 | 4/1995 |
| EP | 645984 A1 | 4/1995 |
| EP | 756735 | 2/1997 |
| EP | 1486900 A1 | 12/2004 |
| EP | 1669033 A1 | 6/2006 |
| GB | 2426200 A | 11/2006 |
| KR | 2005072500 A | 7/2005 |
| KR | 2005084024 A | 8/2005 |
| TW | I231755 B | 5/2005 |
| WO | 9325157 A1 | 12/1993 |
| WO | 9528688 A1 | 10/1995 |
| WO | 0184479 A1 | 11/2001 |
| WO | 2005027755 A1 | 3/2005 |
| WO | 2004049981 A3 | 4/2005 |
| WO | 2005051239 A1 | 6/2005 |
| WO | 2005051240 A1 | 6/2005 |
| WO | 2005084558 A1 | 9/2005 |
| WO | 2006058057 A2 | 6/2006 |
| WO | 2006060795 A1 | 6/2006 |
| WO | 2007041375 A2 | 4/2007 |
| WO | 2007092841 A2 | 8/2007 |
| WO | 2007097854 A2 | 8/2007 |
| WO | 2007145937 A2 | 12/2007 |
| WO | 2008014618 A1 | 2/2008 |
| WO | 2008021494 A2 | 2/2008 |
| WO | 2008112996 | 9/2008 |
| WO | 2008112996 A1 | 9/2008 |
| WO | 2009001083 A1 | 12/2008 |
| WO | 2009045960 A1 | 4/2009 |
| WO | 2009111512 A2 | 9/2009 |

OTHER PUBLICATIONS

Hafez et al., "Computer-assisted Total Knee Arthroplasty Using Patient-Specific Templating", Clinical Orthopaedics and Related Research, 444, 184-192, 2006 (9 pages).

International Preliminary Report on Patentability for International Patent Publication No. PCT/US2008/078143, Apr. 15, 2010, 8 pages.

European Search Report for European Patent Application No. 10150487.6-2310, May 12, 2010, 7 pages.

European Search Report for European Patent Application No. 09171188.7-2310, Sep. 24, 2010, 7 pages.

Search Report for Chinese Application No. 200910179506.2, dated Nov. 11, 2012, 2 pages of unofficial English translation.

Customized Patient Instruments, Patient specific instruments for patient specific needs, brochure. (2008) DePuy Orthopaedics, Inc. 14 sheets.

Customized Patient Instruments, Primary Cruciate Retaining Surgical Technique for use with the Sigma.RTM. Knee System Utilizing Specialist.RTM. 2 Instrumentation, brochure. (2008) DePuy Orthopaedics, Inc. pp. 1-23.

"TruMatch.TM. Personalized knee replacement solutions," tri-fold brochure. (2009) SIGMA.RTM. DePuy Orthopaedics, Inc. 2 pages.

Murphy, S.B., et al. "The Hip Sextant: Navigation of Acetabular Component Orientation Using a Mechanical Instrument," brochure. (2009) 1 page.

(56) References Cited

OTHER PUBLICATIONS

Seel et al., "Three-Dimensional Planning and Virtual Radiographs in Revision Total Hip Arthroplasty for Instability", Clinical Orthopaedics and Related Research, No. 442, pp. 35-38, Jan. 2006.
Radermacher, "Development of a Clinical Demonstrater for Computer Assisted Orthopedic Surgery with CT-Image Based Individual Templates (chapter in Computer Assisted Radiology and Surgery, edited by H.U. Lemke, M.W. Vannier and K. Inamura)," (1997).
Radermacher, "Clinical Experience With the Individual Template Technique," (2001).
Radermacher, "Computer Assisted Orthopedic Surgery by Means of Individual Templates Aspects and Analysis of Potential Applications," (1994).
Radermacher, German Version "Potentials of CT-based Planning and Template-based Procedure in Hip and Knee Surgery," (2000).
Radermacher, English Translation of German Version "Potentials of CT-based Planning and Template-based Procedure in Hip and Knee Surgery," (2000).
PCT Search Report for Application PCT/US2008/078143 (17 pages) dated Dec. 19, 2008.
"Insall/Burstein II Surgical Technique", Constrained Condylar Modular Knee System, Zimmer, (18 pages) (1989).
Berry, Seedhom, et al., "Personalised image-based templates for intra-operative guidance," Proceedings of the Institution of Mechanical Engineers, Part H: Journal of Engineering in Medicine, 111-118, 2005.
Radermacher et al., "Computer-Integrated Orthopaedic Surgery: Connection of Planning and Execution in Surgical Intervention," Computer Integrated Surgery, 451-463, 1995.
Radermacher et al., "CT Image-Based Planning and Execution of Interventions in Orthopedic Surgery Using Individual Templates—Experimental Results and Aspects of Clinical Applications," Computer Assisted Orthopaedic Surgery, L.P Nolte and R. Ganz, eds, 42-52, Hogrefe & Huber Publishing 1999.
PCT Search Report for International Application No. PCT/US2011/044466, filed Jul. 19, 2011, 4 pages.

\* cited by examiner

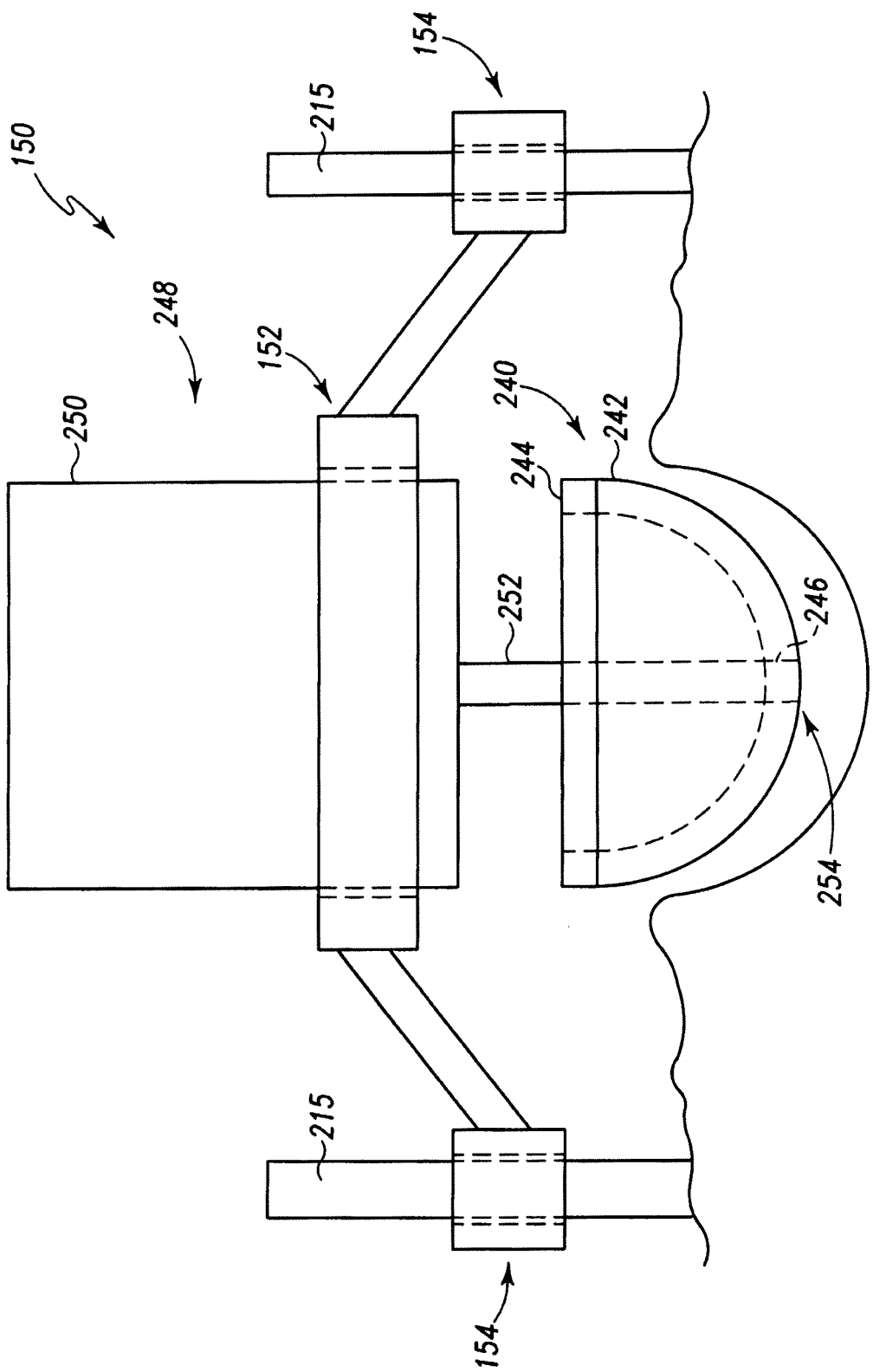

CUSTOMIZED PATIENT-SPECIFIC ACETABULAR ORTHOPAEDIC SURGICAL INSTRUMENT AND METHOD OF USE AND FABRICATION

CROSS-REFERENCE TO RELATED U.S. PATENT APPLICATIONS

This application claims priority under 35 U.S.C. §119(e) to U.S. Provisional Patent Application Ser. No. 61/101,524 entitled "Customized Patient-specific Acetabular Orthopaedic Surgical Instrument and Method of Fabrication," by Ryan Keefer, which was filed on Sep. 30, 2008, the entirety of which is hereby incorporated by reference.

TECHNICAL FIELD

The present disclosure relates generally to customized patient-specific orthopaedic surgical instruments and more particularly to customized patient-specific acetabular orthopaedic surgical instruments.

BACKGROUND

Joint arthroplasty is a well-known surgical procedure by which a diseased and/or damaged natural joint is replaced by a prosthetic joint. For example, in a hip arthroplasty surgical procedure, a prosthetic hip replaces a patient's natural hip. A typical prosthetic hip includes an acetabular orthopaedic prosthesis and/or femoral head orthopaedic prosthesis. A typical acetabular orthopaedic prosthesis includes an acetabular cup, which is secured to the patient's natural acetabulum, and an associated polymer bearing or ring.

To facilitate the replacement of the natural joint with an acetabular orthopaedic prosthesis, orthopaedic surgeons may use a variety of orthopaedic surgical instruments such as, for example, reamers, drill guides, drills, and/or other surgical instruments. Typically, such orthopaedic surgical instruments are generic with respect to the patient such that the same orthopaedic surgical instrument may be used on a number of different patients during similar orthopaedic surgical procedures.

SUMMARY

According to one aspect, a customized patient-specific orthopaedic instrument for facilitating implantation of an acetabular cup prosthesis in a coxal bone of a patient may include a customized patient-specific acetabular reaming guide. The customized patient-specific acetabular reaming guide may include a body having a longitudinal passageway defined therethrough. The customized patient-specific acetabular reaming guide may also include a plurality of arms extending from the body. Additionally, the customized patient-specific acetabular reaming guide may include a plurality of feet configured to contact a coxal bone of a patient. Each foot of the plurality of feet may be coupled to a corresponding arm of the plurality of arms. Additionally, each foot of the plurality of feet may be positioned relative to the body based on a predetermined degree of version and inclination angles of the acetabular cup prosthesis when implanted in the patient's coxal bone and on the contour of the coxal bone of the patient.

In some embodiments, each foot of the plurality of feet may include a bottom, bone-facing surface having a customized patient-specific negative contour configured to receive a portion of the patient's coxal bone having a corresponding positive contour. Additionally, in some embodiments, the longitudinal passageway of the body may be sized to receive a bone guide pin. Alternatively, the longitudinal passageway of the body may be sized to receive a body of an acetabular reamer surgical tool.

In some embodiments, the body may include a bottom, bone-facing surface and each foot of the plurality of feet may include a top surface. The bottom, bone-facing surface of the body may be coplanar or non-coplanar with respect to a plane defined by the top surface of least one of the plurality of feet. In some embodiments, the plurality of feet includes a first foot having a first top surface defining a first plane and a second foot having a second top surface defining a second plane. In such embodiments, the bottom, bone-facing surface of the body, the first top surface, and the second top surface may be parallel and non-coplanar with respect to each other. Additionally, in some embodiments, each foot of the plurality of feet may include a bottom surface. The bottom, bone-facing surface of the body may positioned medially with respect to the bottom surface of each foot of the plurality of feet when the customized patient-specific acetabular reaming guide is positioned in contact with the patient's coxal bone.

Additionally, in some embodiments, each foot of the plurality of feet may have a longitudinal length substantially different from each other. The body may also include a sidewall and each arm of the plurality of arms may include a bottom surface. Each bottom surface of the plurality of arms may define an angle with respect to the sidewall of the body that is different in magnitude with respect to the angle defined by each other bottom surface of the plurality of arms. Additionally, in some embodiments, an angle may be defined between each arm of the plurality of arms with respect to another adjacent arm of the plurality of arms when viewed in the top plan view. Each of such angles may be different in magnitude from each other. Additionally, each foot of the plurality of feet may be spaced apart from the body, when viewed in the top plan view, a distance different in magnitude with respect to the distance defined by each other foot of the plurality of feet.

In some embodiments, each arm of the plurality of arms may be coupled to the body via a joint such that each arm is movable relative to the body. Additionally or alternatively, each foot of the plurality of feet may be coupled to the corresponding arm via a joint such that each foot is movable relative to the corresponding arm. In some embodiments, the plurality of arms may comprise at least three arms extending from the body. Additionally, in some embodiments, each foot of the plurality of feet may include a longitudinal passageway defined therein, each of the longitudinal passageways of the plurality of feet being sized to receive a bone guide pin.

According to another aspect, a customized patient-specific orthopaedic instrument for facilitating implantation of an acetabular cup prosthesis in a coxal bone of a patient may include a customized patient-specific acetabular reaming guide. The customized patient-specific acetabular reaming guide may include a body having a longitudinal passageway defined therethrough, a plurality of arms coupled to the body via corresponding joints such that each arm of the plurality of arms is separately movable with respect to the body and a plurality of feet configured to contact a coxal bone of a patient. Each foot of the plurality of feet may be coupled to a corresponding arm of the plurality of arms via a corresponding joint such that each foot of the plurality of feet is separately movable with respect to the body. Additionally each foot of the plurality of feet may include a bottom, bone-facing surface having a customized patient-specific negative contour configured to receive a portion of the patient's coxal bone having a corresponding positive contour. In some embodiments, each foot of the plurality of feet may include a longitudinal passageway defined therein, each of the longitudinal passageways of the plurality of feet being sized to receive a bone guide pin.

According to a further aspect, a method for performing an orthopaedic bone reaming procedure on a patient's acetabulum to facilitate implantation of an acetabular cup prosthesis in a coxal bone of the patient may include positioning a customized patient-specific acetabular reaming guide on the patient's coxal bone. The customized patient-specific acetabular reaming guide may include a body having a longitudinal passageway defined therethrough and a plurality of feet coupled to the body and configured to contact the coxal bone of the patient. Each foot of the plurality of feet may be positioned relative to the body based on a predetermined degree of version and inclination angles of the acetabular cup prosthesis when implanted in the patient's coxal bone.

The method may also include drilling a pilot hole into the patient's acetabulum using the longitudinal passageway of the body as a drill guide. Additionally, the method may include inserting a bone guide pin into the pilot hole formed in the patient's acetabulum. The method may further include advancing a cannulated acetabular reamer over the guide pin. The method may also include reaming the patient's acetabulum with the cannulated acetabular reamer using the bone guide pin as a guide for the cannulated reamer.

According to yet a further aspect, a method for performing an orthopaedic bone reaming procedure on a patient's acetabulum to facilitate implantation of an acetabular cup prosthesis in a coxal bone of the patient may include positioning a customized patient-specific acetabular reaming guide on the patient's coxal bone. The customized patient-specific acetabular reaming guide may include a body having a longitudinal passageway defined therethrough and a plurality of feet configured to contact the coxal bone of the patient. Each foot of the plurality of feet may be coupled to the body and may have a longitudinal passageway defined therethrough. Each foot of the plurality of feet may be positioned relative to the body based on a predetermined degree of version and inclination angles of the acetabular cup prosthesis when implanted in the patient's coxal bone.

The method may include drilling a plurality of pilot holes into the patient's coxal bone using the longitudinal passageways of the plurality of feet as drill guides. The method may also include inserting a bone guide pin through each longitudinal passageway of the plurality of feet and into each of the corresponding pilot holes formed in the patient's coxal bone. Additionally, the method may include securing an acetabular reamer within the longitudinal passageway of the body. The method may further include reaming the patient's acetabulum with the acetabular reamer using the plurality of guide pins as guides for the acetabular reamer.

BRIEF DESCRIPTION OF THE DRAWINGS

The detailed description particularly refers to the following figures, in which:

FIG. 21 is a side elevation view of an acetabular prosthesis positioned for implantation using the customized patient-specific acetabular orthopaedic surgical instrument of FIG. 12 or FIG. 16.

DETAILED DESCRIPTION OF THE DRAWINGS

Figure 1:
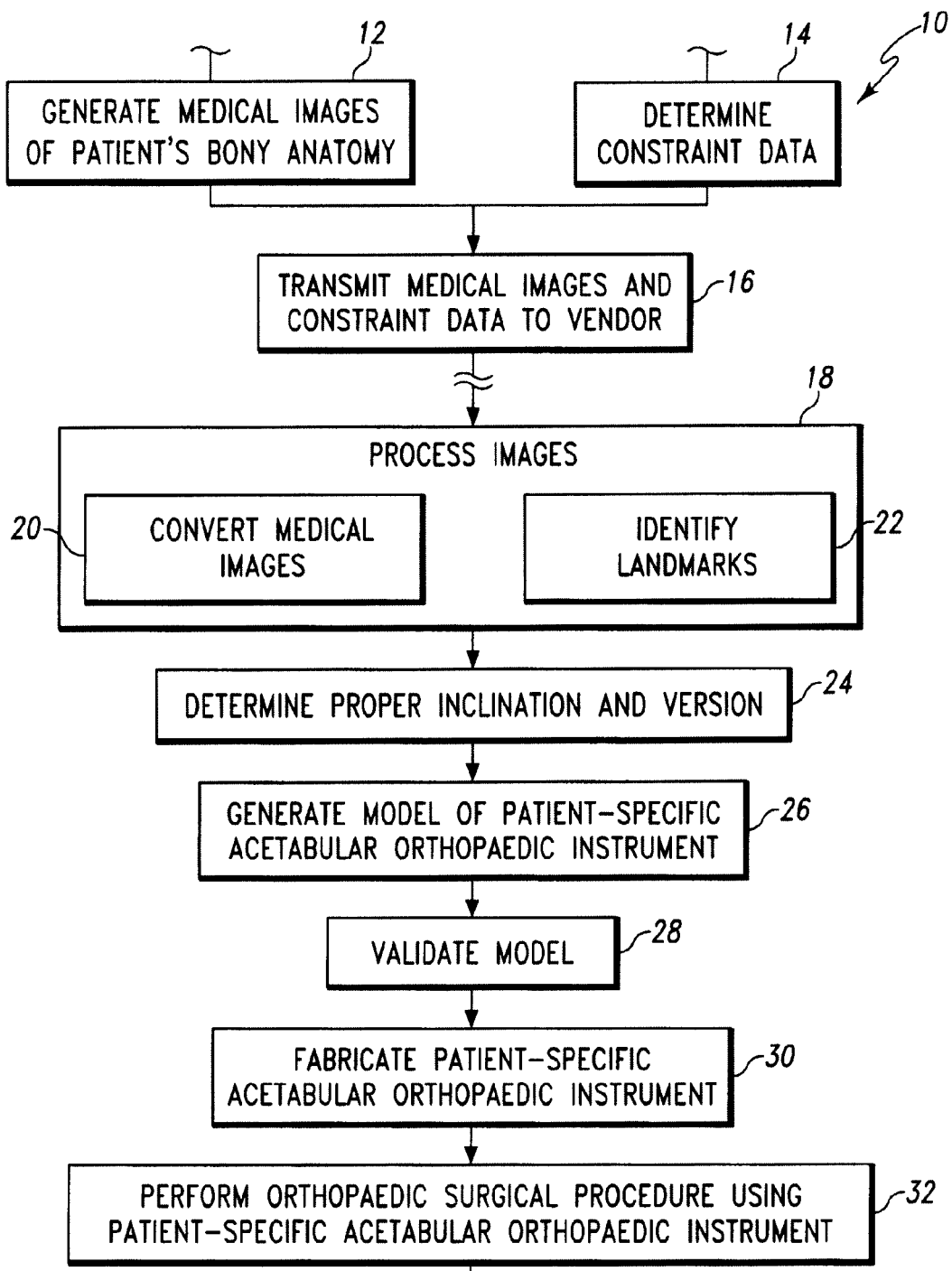
FIG. 1 is a simplified flow diagram of a method for designing and fabricating a customized patient-specific acetabular orthopaedic surgical instrument.

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring to FIG. 1, an algorithm 10 for fabricating a customized patient-specific orthopaedic surgical instrument is illustrated. What is meant herein by the term "customized patient-specific orthopaedic surgical instrument" is a surgical tool for use by a surgeon in performing an orthopaedic surgical procedure that is intended, and configured, for use on a particular patient. As such, it should be appreciated that, as used herein, the term "customized patient-specific orthopaedic surgical instrument" is distinct from standard, non-patient specific orthopaedic surgical instruments that are intended for use on a variety of different patients. Additionally, it should be appreciated that, as used herein, the term "customized patient-specific orthopaedic surgical instrument" is distinct from orthopaedic prostheses, whether patient-specific or generic, which are surgically implanted in the body of the patient. Rather, customized patient-specific orthopaedic surgical instruments are used by an orthopaedic surgeon to assist in the implantation of orthopaedic prostheses.

In some embodiments, the customized patient-specific acetabular orthopaedic surgical instrument may be customized to the particular patient based on the location at which the instrument is to be coupled to one or more bones of the patient, such as in an area of the patient's coxal bone proximate to the acetabulum. For example, in some embodiments, the customized patient-specific acetabular orthopaedic surgical instrument may include one or more bone-contacting or facing surfaces having a negative contour that matches the contour of a portion of the relevant bone of the patient, which is discussed in more detail below in regard to FIG. 5. As such, the customized patient-specific acetabular orthopaedic surgical instrument is configured to be coupled to the patient's coxal bone in a unique location and position with respect to the patient's bony anatomy. That is, the negative contours of the bone-contacting surfaces are configured to receive a matching contour surface of the portion of the patient's coxal bone. As such, the orthopaedic surgeon's guesswork and/or intra-operative decision-making with respect to the placement of the patient-specific acetabular orthopaedic surgical instrument are reduced. For example, the orthopaedic surgeon may not be required to locate landmarks of the patient's bone to facilitate the placement of the patient-specific acetabular orthopaedic surgical instrument, which typically requires some amount of estimation on part of the surgeon. Rather, the orthopaedic surgeon may simply couple the customized patient-specific acetabular orthopaedic surgical instrument to the patient's coxal bone in the unique location. When so coupled, the patient-specific acetabular orthopaedic surgical instrument defines a particular degree of version and inclination angles relative to the acetabulum and the intended acetabular orthopaedic prosthesis.

As shown in FIG. 1, the method 10 includes process steps 12 and 14, in which an orthopaedic surgeon performs pre-operative planning of the acetabular orthopaedic surgical procedure to be performed on a patient. The process steps 12 and 14 may be performed in any order or contemporaneously with each other. In process step 12, a number of medical images of the patient's acetabulum and the surrounding bony anatomy are generated. To do so, the orthopaedic surgeon or other healthcare provider may operate an imaging system to generate the medical images. The medical images may be embodied as any number and type of medical images capable of being used to generate a three-dimensional rendered model of the patient's acetabulum and surrounding bony anatomy. For example, the medical images may be embodied as any number of computed tomography (CT) images, magnetic resonance imaging (MRI) images, or other three-dimensional medical images. Additionally, or alternatively, as discussed in more detail below in regard to process step 18, the medical images may be embodied as a number of X-ray images or other two-dimensional images from which a three-dimensional rendered model of the area of the patient's coxal bone proximate to the acetabulum and the surrounding bony anatomy may be generated.

In process step 14, the orthopaedic surgeon may determine any additional pre-operative constraint data. The constraint data may be based on the orthopaedic surgeon's preferences, preferences of the patient, anatomical aspects of the patient, guidelines established by the healthcare facility, or the like. For example, the constraint data may include the orthopaedic surgeon's preference for the amount of inclination and version for the acetabular prosthesis, the amount of the bone to ream, the size range of the orthopaedic implant, and/or the like. In some embodiments, the orthopaedic surgeon's preferences are saved as a surgeon's profile, which may be used as a default constraint values for further surgical plans.

In process step 16, the medical images and the constraint data, if any, are transmitted or otherwise provided to an orthopaedic surgical instrument vendor or manufacturer. The medical images and the constraint data may be transmitted to the vendor via electronic means such as a network or the like. After the vendor has received the medical images and the constraint data, the vendor processes the images in step 18. The orthopaedic surgical instrument vendor or manufacturer process the medical images to facilitate the determination of the proper planes of inclination and version, implant sizing, and fabrication of the customized patient-specific acetabular orthopaedic surgical instrument as discussed in more detail below.

In process step 20, the vendor may convert or otherwise generate three-dimensional images from the medical images. For example, in embodiments wherein the medical images are embodied as a number of two-dimensional images, the vendor may use a suitable computer algorithm to generate one or more three-dimensional images form the number of two-dimensional images. Additionally, in some embodiments, the medical images may be generated based on an established standard such as the Digital Imaging and Communications in Medicine (DICOM) standard. In such embodiments, an edge-detection, thresholding, watershed, or shape-matching algorithm may be used to convert or reconstruct images to a format acceptable in a computer aided design application or other image processing application.

In process step 22, the vendor may process the medical images, and/or the converted/reconstructed images from process step 20, to determine a number of aspects related to the bony anatomy of the patient such as the anatomical axis of the patient's bones, the mechanical axis of the patient's bone, other axes and various landmarks, and/or other aspects of the patient's bony anatomy. To do so, the vendor may use any suitable algorithm to process the images.

In process step 24, the desired inclination and version planes for implantation of the acetabular orthopaedic prosthesis are determined. The planned inclination and version planes may be determined based on the type, size, and position of the acetabular orthopaedic prosthesis to be used during the orthopaedic surgical procedure; the process images, such as specific landmarks identified in the images; and the constraint data supplied by the orthopaedic surgeon in process steps 14 and 16. The type and/or size of the acetabular orthopaedic prosthesis may be determined based on the patient's anatomy and the constraint data. For example, the constraint data may dictate the type, make, model, size, or other characteristic of the acetabular orthopaedic prosthesis. The selection of the acetabular orthopaedic prosthesis may also be modified based on the medical images such that an acetabular orthopaedic prosthesis that is usable with the acetabulum of the patient and that matches the constraint data or preferences of the orthopaedic surgeon is selected.

In addition to the type and size of the acetabular orthopaedic prosthesis, the planned location and position of the acetabular orthopaedic prosthesis relative to the patient's bony anatomy is determined. To do so, a digital template of the acetabular orthopaedic prosthesis may be overlaid onto one or more of the processed medical images. The vendor may use any suitable algorithm to determine a recommended location and orientation of the acetabular orthopaedic prosthesis (i.e., the digital template) with respect to the patient's bone based on the processed medical images (e.g., landmarks of the patient's acetabulum defined in the images) and/or the constraint data. Additionally, any one or more other aspects of the patient's bony anatomy may be used to determine the proper positioning of the digital template.

In some embodiments, the digital template along with surgical alignment parameters may be presented to the orthopaedic surgeon for approval. The approval document may include the implant's planned inclination and version planes, the orientation of the transverse acetabular ligament and labrum, and other relevant landmarks of the patient's bony anatomy.

The proper inclination and version planes for the acetabular orthopaedic prosthesis may then be determined based on the determined size, location, and orientation of the acetabular orthopaedic prosthesis. In addition, other aspects of the patient's bony anatomy, as determined in process step 22, may be used to determine or adjust the planned inclination and version planes. For example, the determined mechanical axis, landmarks, and/or other determined aspects of the relevant bones of the patient may be used to determine the planned inclination and version planes.

In process step 26, a model of the customized patient-specific acetabular orthopaedic surgical instrument is generated. In some embodiments, the model is embodied as a three-dimensional rendering of the customized patient-specific acetabular orthopaedic surgical instrument. In other embodiments, the model may be embodied as a mock-up or fast prototype of the customized patient-specific acetabular orthopaedic surgical instrument. The patient-specific acetabular orthopaedic surgical instrument to be modeled and fabricated may be determined based on the acetabular orthopaedic surgical procedure to be performed, the constraint data, and/or the type of orthopaedic prosthesis to be implanted in the patient.

The particular shape of the customized patient-specific acetabular orthopaedic surgical instrument is determined based on the planned location and implantation angles of the acetabular orthopaedic prosthesis relative to the patient's acetabulum. The planned location of the customized patient-specific acetabular orthopaedic surgical instrument relative to the patient's acetabulum may be selected based on, in part, the planned inclination and version planes of the patient's acetabulum as determined in step 24. For example, in some embodiments, the customized patient-specific acetabular orthopaedic surgical instrument is embodied as an acetabular reamer guide. In such embodiments, the location of the acetabular reamer guide is selected such that the acetabular reamer guide is usable to position the acetabular orthopaedic prosthesis at the planned inclination and version planes determined in process step 24. Additionally, the planned location of the orthopaedic surgical instrument may be based on the identified landmarks of the patient's acetabulum identified in process step 22.

In some embodiments, the particular shape or configuration of the customized patient-specific acetabular orthopaedic surgical instrument may be determined based on the planned location of the instrument relative to the patient's bony anatomy. That is, the customized patient-specific acetabular orthopaedic surgical instrument may include a bone-contacting surface having a negative contour that matches the corresponding contour of a portion of the bony anatomy of the patient such that the orthopaedic surgical instrument may be coupled to the bony anatomy of the patient in a unique location, which corresponds to the pre-planned location for the instrument. When the orthopaedic surgical instrument is coupled to the patient's bony anatomy in the unique location, one or more guides (e.g., cutting or drilling guide) of the orthopaedic surgical instrument may be aligned to the inclination and version planes, as discussed above.

After the model of the customized patient-specific acetabular orthopaedic surgical instrument has been generated in process step 26, the model is validated in process step 28. The model may be validated by, for example, analyzing the rendered model while coupled to the three-dimensional model of the patient's anatomy to verify the correlation of reaming guides, inclination and version planes, and/or the like. Additionally, the model may be validated by transmitting or otherwise providing the model generated in step 26 to the orthopaedic surgeon for review. For example, in embodiments wherein the model is a three-dimensional rendered model, the model along with the three-dimensional images of the patient's acetabulum and area of the coxal bone proximate to the acetabulum may be transmitted to the surgeon for review. In embodiments wherein the model is a physical prototype, the model may be shipped to the orthopaedic surgeon for validation.

After the model has been validated in process step 28, the customized patient-specific acetabular orthopaedic surgical instrument is fabricated in process step 30. The customized patient-specific acetabular orthopaedic surgical instrument may be fabricated using any suitable fabrication device and method. Additionally, the customized patient-specific acetabular orthopaedic instrument may be formed from any suitable material such as a metallic material, a plastic material, or combination thereof depending on, for example, the intended use of the instrument. The fabricated customized patient-specific acetabular orthopaedic instrument is subsequently shipped or otherwise provided to the orthopaedic surgeon. The surgeon performs the orthopaedic surgical procedure in process step 32 using the customized patient-specific acetabular orthopaedic surgical instrument. As discussed above, because the orthopaedic surgeon does not need to determine the proper location of the orthopaedic surgical instrument intra-operatively, which typically requires some amount of estimation on part of the surgeon, the guesswork and/or intra-operative decision-making on part of the orthopaedic surgeon is reduced.

It should also be appreciated that variations in the bony of anatomy of the patient may require more than one customized patient-specific acetabular orthopaedic surgical instrument to be fabricated according to the method described herein. For example, the patient may require the implantation of two acetabular orthopaedic prostheses to replace both natural hips. As such, the surgeon may follow the method 10 of FIG. 1 to fabricate a different customized patient-specific acetabular orthopaedic surgical instrument for use in replacing each natural hip. Each customized patient-specific acetabular orthopaedic surgical instrument defines a particular degree of version and inclination angles relative to each particular acetabulum that is different due to the variation in the bony anatomy of each hip.

Figure 2:
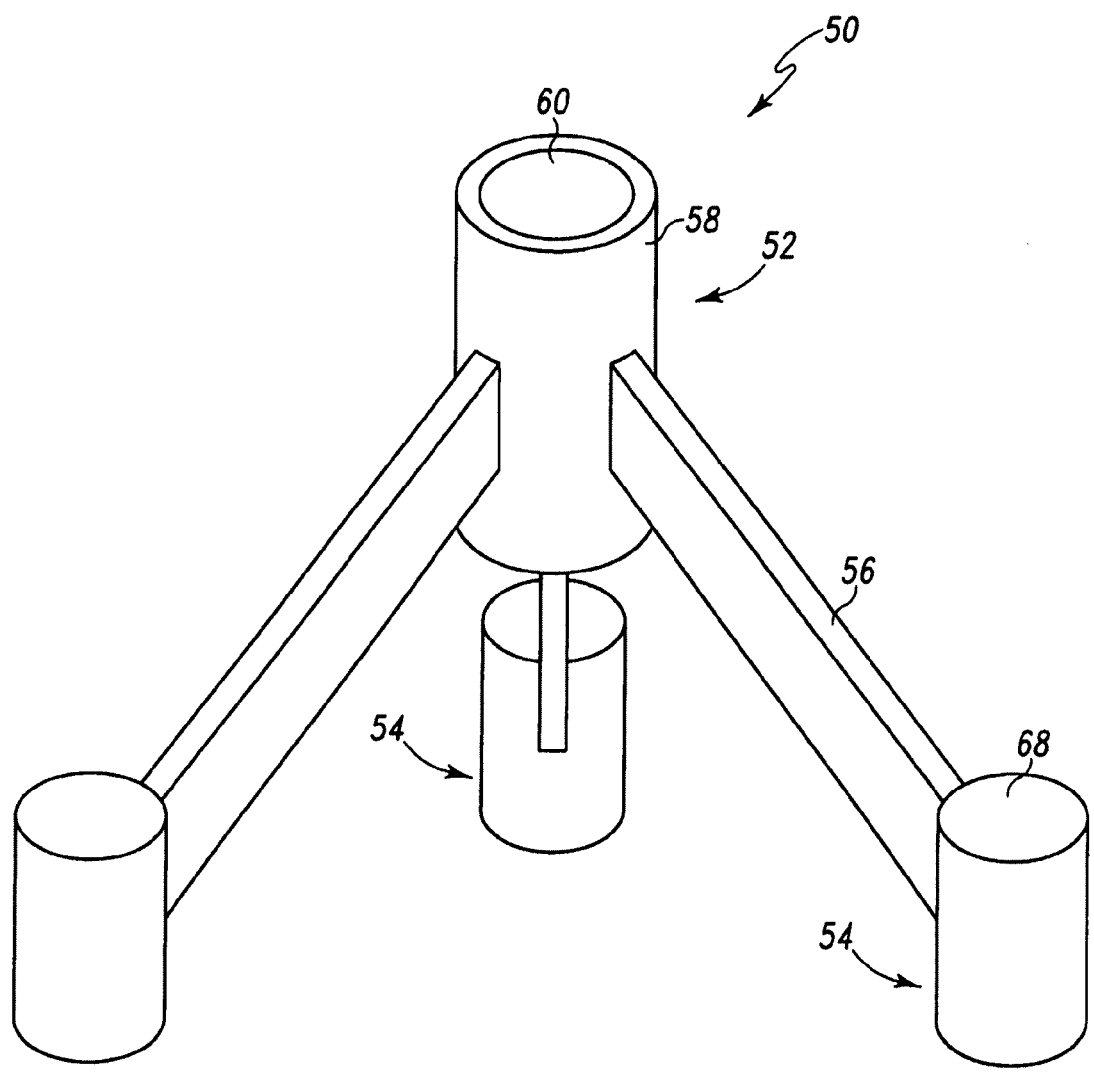
FIG. 2 is a perspective view of one embodiment of a customized patient-specific acetabular orthopaedic surgical instrument.
Figure 3:
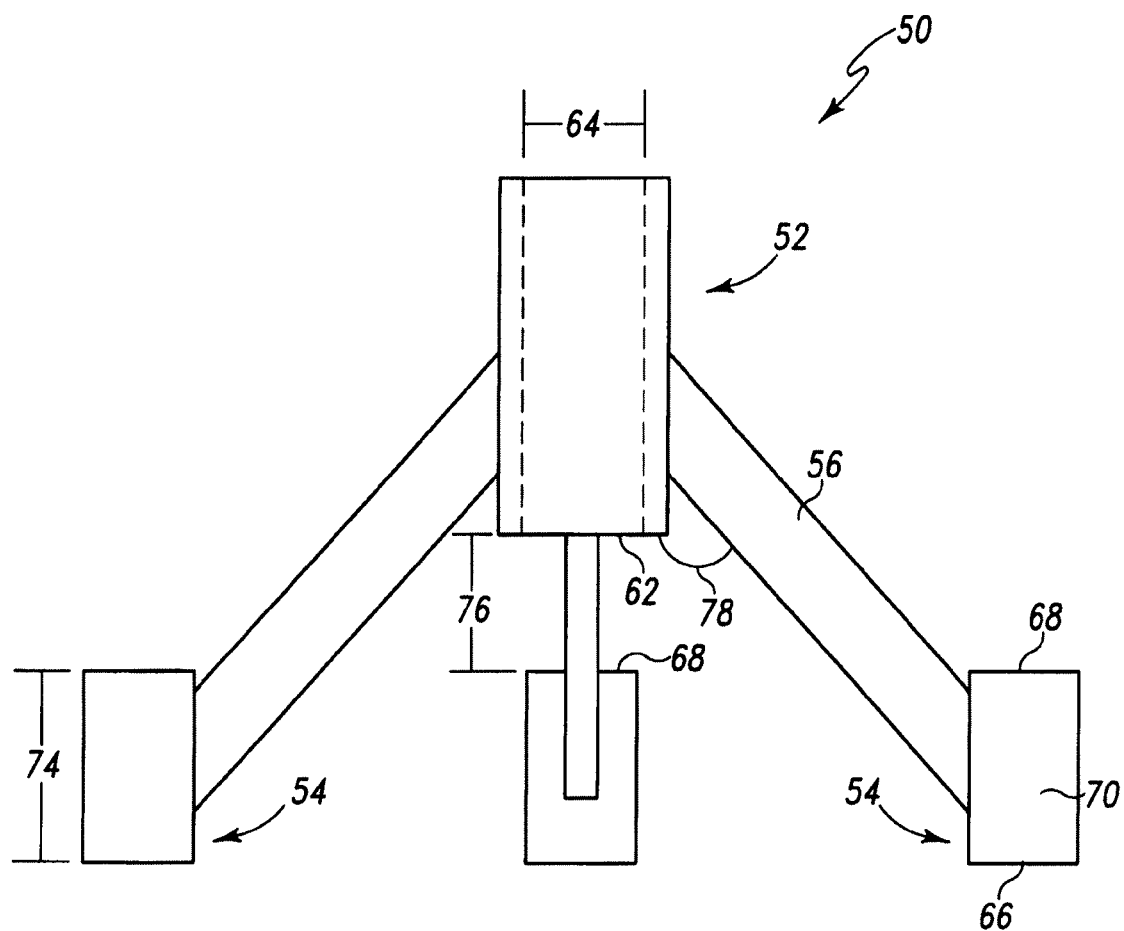
FIG. 3 is a side elevation view of the customized patient-specific acetabular orthopaedic surgical instrument of FIG. 2.
Figure 4:
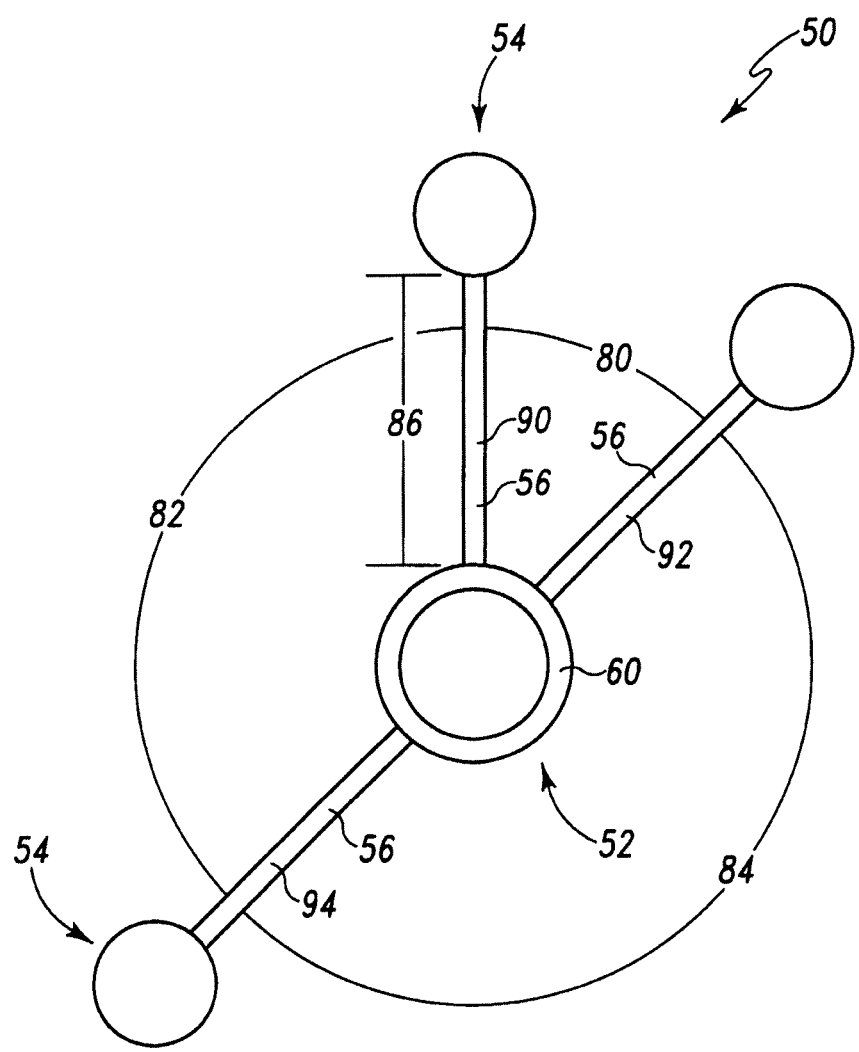
FIG. 4 is a top plan view of the customized patient-specific acetabular orthopaedic surgical instrument of FIG. 2.

Referring now to FIGS. 2-4, in one embodiment, the customized patient-specific acetabular orthopaedic surgical instrument may be embodied as an acetabular reamer guide 50. The acetabular reamer guide 50 is usable by a surgeon to secure a bone guide pin to the patient's acetabulum in a predetermined location and orientation that will position the acetabular orthopaedic prosthesis at the desired, predetermined angles of inclination and version. The bone guide pin is subsequently used to orient and guide a cannulated reamer as discussed in more detail below.

The illustrative acetabular reamer guide 50 includes a drill guide 52 and a plurality of mounting feet 54. Each of the mounting feet 54 is coupled to the drill guide 52 via a corresponding arm 56. In the illustrative embodiment of FIGS. 2-4, the arms 56, mounting feet 54, and drill guide 52 are each formed from separate pieces. For example, the arms 56 may be secured to the mounting feet 54 and/or the drill guide 52 via suitable fasteners such as screws, bolts, adhesive, or the like. It should be appreciated that in other embodiments the drill guide 52, mounting feet 54, and arms 56 could be formed as a monolithic component. The drill guide 52, mounting feet 54, and arms 56 may be formed from any suitable material such as a resilient plastic or metallic material. In one particular embodiment, the acetabular reamer guide 50 is formed from an implant-grade metallic material such as titanium or cobalt chromium.

The drill guide 52 includes a body 58 having a drill guide longitudinal passageway 60 defined therethrough and a bottom surface 62. In the illustrative embodiment of FIG. 2, the body 58 has a substantially cylindrical shape but may have other shapes in other embodiments. For example, in some embodiments, the body 58 may have a substantially rectangular, triangular, or polygonal cross-section. The longitudinal passageway 60 is sized such that a bone guide pin is insertable through the passageway 60 to allow the guide pin to be secured to the patient's acetabulum. For example, the passageway 60 may have an inner diameter 64 (see FIG. 3) that is slightly larger than the outer diameter of the guide pin. Additionally, the passageway 60 may have any cross-sectional shape suitable for receiving a drill bit of a bone drill and guide pin therethrough. For example, in FIGS. 2-4 the passageway 60 has a substantially circular cross-section, but in other embodiments, the body 58 may include a passageway 60 configured to receive a guide pin with a different cross-sectional shape.

Figure 5:
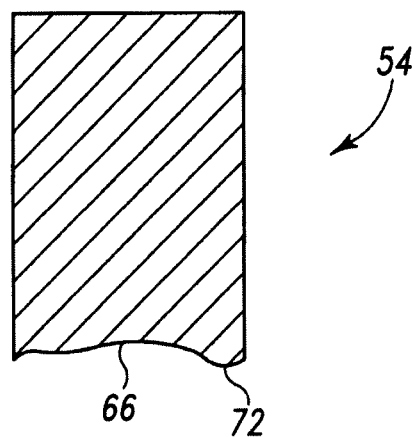
FIG. 5 is a cross-sectional view of one embodiment of a mounting foot of the customized patient-specific acetabular orthopaedic surgical instrument of FIG. 2.

Each of the mounting feet 54 is configured to contact the patient's bony anatomy during use. In the illustrative embodiment of FIGS. 2-4, each of the mounting feet 54 is substantially cylindrical in shape but may have other shapes in other embodiments. For example, in some embodiments, the mounting feet 54 may have a substantially rectangular, triangular, or polygonal cross-section. Each of the mounting feet 54 includes a bottom surface 66, which is configured to contact a portion of the area of the patient's coxal bone proximate to the acetabulum. Each mounting foot 54 also includes a top surface 68 opposite the bottom surface 66 and a sidewall 70. As discussed in greater detail below, the position of each mounting foot 54 relative to the drill guide 52 and relative to each other allows the acetabular reamer guide 50 to be coupled to the patient's coxal bone in a substantially unique orientation and location based on the contour of the patient's coxal bone. Additionally, in some embodiments, the bottom surface 66 of each mounting foot 54 may be customized to the contour of the patient's acetabulum. For example, as illustrated in FIG. 5, the bottom surfaces 66 of the mounting feet 54 are configured with a customized patient-specific negative contour 72 configured to receive a portion of the corresponding contour of the patient's coxal bone proximate to the acetabulum. As such, the acetabular reamer guide 50 is configured to be coupled to the patient's coxal bone in a desired position and orientation, which has been predetermined to establish the desired inclination and version planes of the acetabular orthopaedic prosthesis.

Each of the mounting feet 54 has a longitudinal length 74, which may be determined based on the surface contour of the patient's bony anatomy such that the acetabular reamer guide 50 is positioned at the desired angles of inclination and version. For example, in the illustrative embodiment of FIG. 3, the length 74 of each mounting foot 54 is equal to one another. In other embodiments, the length 74 may be different relative to each mounting foot 54 to position the reamer guide 50 at the desired angles of inclination and version.

In some embodiments, as illustrated in FIG. 3, the bottom surface 62 of the drill guide 52 may be offset a distance 76 from the top surface 68 of each mounting foot 54. That is, the bottom surface 62 may be non-coplanar with the top surface 68 of one or more of the mounting feet 54. In the illustrative embodiment of FIG. 3, the distance 76 for each mounting foot 54 is equal. In other embodiments, the distance 76 may be different such that the acetabular reamer guide 50 is positioned in the planned orientation and location, which has been predetermined to establish the desired inclination and version planes of the acetabular orthopaedic prosthesis. Additionally, in other embodiments, the bottom surface 62 of the drill guide 52 may be coplanar with the top surface 68 of each mounting foot 54 such that the distance 76 is equal to zero. Further, in some embodiments, the drill guide 52 may extend downwardly such that the bottom surface 62 of the drill guide 52 is substantially equal to, higher than, or lower than the bottom surfaces 66 of the mounting feet 54. For example, in some embodiments, the bottom surface 62 of the drill guide 52 may be positioned medially relative to the mounting feet 54 when the acetabular reaming guide 50 is coupled to the patient's coxal bone.

As discussed above, the arms 56 secure the mounting feet 54 to the drill guide 52. In the illustrative embodiment, the arms 56 are embodied as rectangular shafts, but may have other shapes and configurations in other embodiments. For example, the arms 56 may be straight, curved or bowed, angled, or the like in other embodiments. When viewed from the side elevation perspective of FIG. 3, an angle 78 is defined between a bottom surface of each arm 56 and the bottom surface 62 of drill guide 52. In the illustrative embodiment, each angle 78 is equal to one another. In other embodiments, each angle 78 may be different depending on the patient's anatomy and the desired angles of inclination and version of the acetabular orthopaedic prosthesis. Additionally, when viewed from the top plan of FIG. 4, each arm 56 extends a distance 86 from the drill guide 52. It should be appreciated that in the illustrative embodiment of FIG. 4, the arms 56 extend the same distance 86 from the drill guide 52. However, in other embodiments, the arms 56 may each extend a distance 86 that is different from one another depending on the patient's anatomy and the desired angles of inclination and version of the acetabular orthopaedic prosthesis.

Further, when viewed from the top plan view of FIG. 4, the arms 56 extend from drill guide 52 in a configuration so as to define a number of different angles 80, 82, and 84. For example, as illustrated in FIG. 4, an arm 90 and an arm 92 define an angle 80 therebetween, an arm 90 and an arm 94 define an angle 82 therebetween, and the arm 92 and the arm 94 define an angle 84 therebetween. In some embodiments, as shown in FIG. 4, the magnitude of angle 84 is greater than the magnitude of angle 82, which is greater than the magnitude of angle 80. Like many other dimensional characteristics described herein, the magnitude of the angles 80, 82, and 84 may be customized to any degree required for the particular patient. In some embodiments, the arms 56 may extend from the drill guide 52 in a substantially uniform configuration such that the angle defined between each arm is substantially equal.

Figure 6:
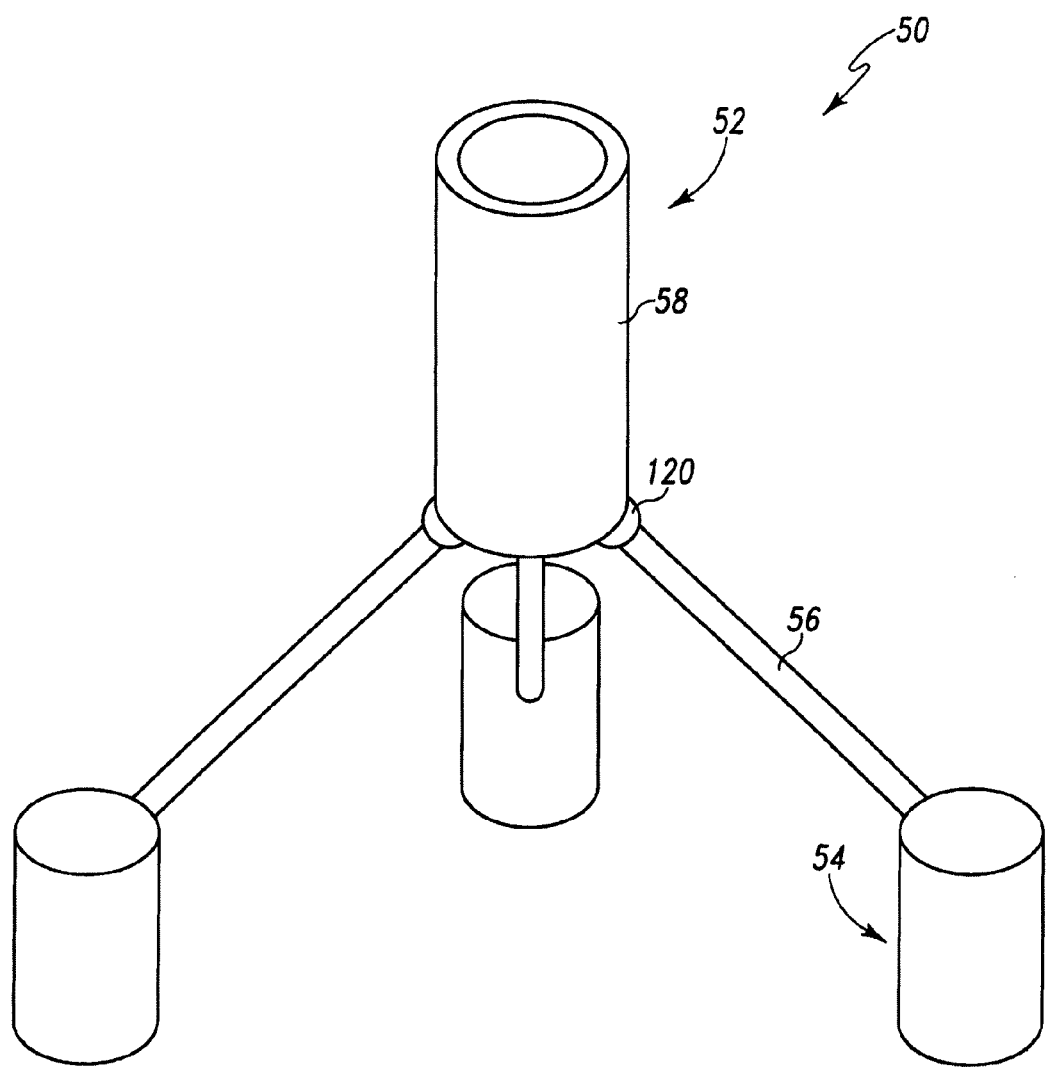
FIG. 6 is a perspective view of another embodiment of a customized patient-specific acetabular orthopaedic surgical instrument.
Figure 7:
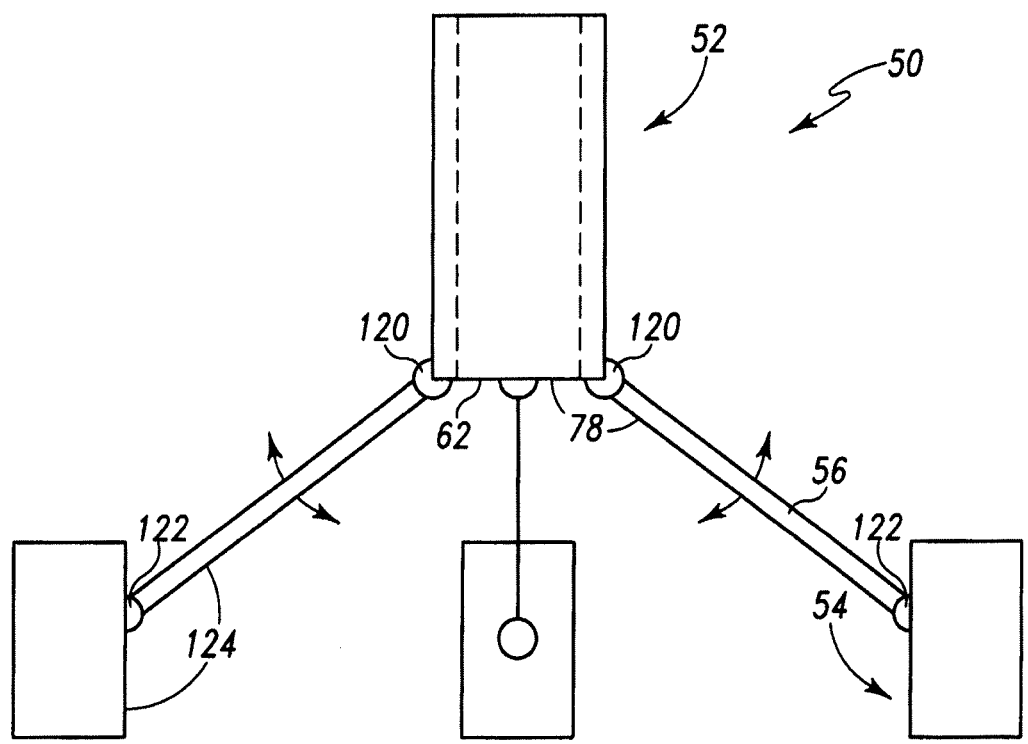
FIG. 7 is a side elevation view of the customized patient-specific acetabular orthopaedic surgical instrument of FIG. 6.
Figure 8:
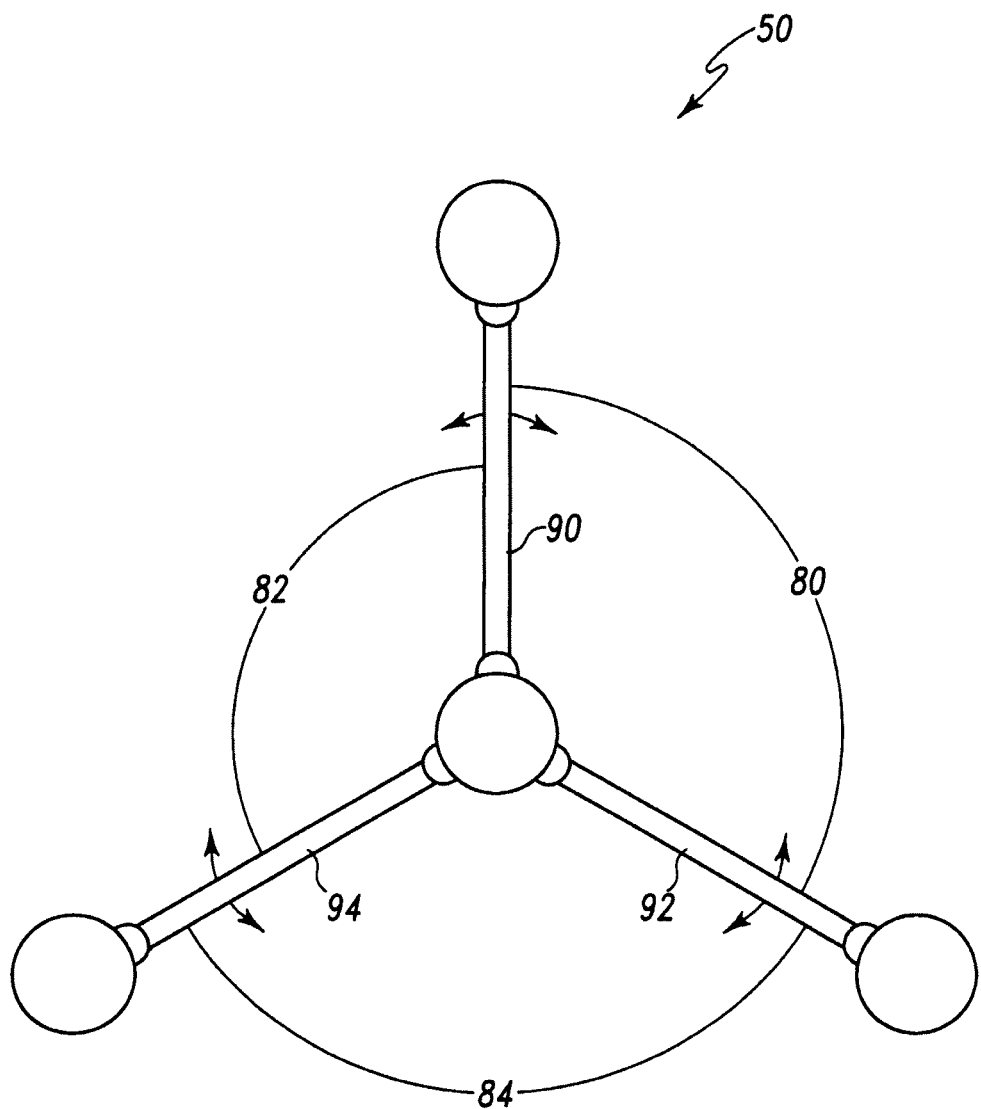
FIG. 8 is a top plan view of the customized patient-specific acetabular orthopaedic surgical instrument of FIG. 6.

Referring now to FIGS. 6-8, in another embodiment, the acetabular reamer guide 50 is adjustable by the surgeon pre-operatively or interoperatively. Some features of the embodiment illustrated in FIGS. 6-8 are substantially similar to those discussed above in reference to the embodiment of FIGS. 2-4. Those features that are substantially similar have the same reference numbers as designated in the embodiment of FIGS. 2-4.

In the illustrative embodiment of FIGS. 6-8, each arm 56 is moveably coupled to the drill guide 52 and each mounting foot 54. In particular, each arm 56 is secured to a joint 120 of drill guide 52 and a corresponding joint 122 of each mounting foot 54. The joints 120, 122 may be embodied as hinges, universal joints, or the like configured to allow positioning of the mounting feet 54 relative to the drill guide 52. The joints 120, 122 may include a locking mechanism (not shown) capable of fixing each arm 56 at a desired position. It will be appreciated that in other embodiments not all arms 56 may be moveably secured to the drill guide 52 and/or mounting feet 54. Additionally, the acetabular reamer guide 50 may include any combination of joints to position the acetabular reamer guide 50 at the planned orientation and location to establish the desired inclination and version planes of the acetabular orthopaedic prosthesis.

It should be appreciated that the acetabular reamer guide 50 is adjustable by the orthopaedic surgeon to improve the coupling of the guide 50 to the patient's bony anatomy. For example, when viewed from the side elevation perspective of FIG. 7, each angle 78 defined between the bottom surface 62 of the drill guide 52 and each arm 56 is adjustable to position the acetabular reamer guide 50 at the planned orientation and location. Additionally, an angle 124 is defined between each arm 56 and the sidewall 70 of each mounting foot 54. In the illustrative embodiment of FIG. 7, the angle 124 is adjustable to position the acetabular reamer guide 50 at the desired location and orientation. In other embodiments, each angle 124 may or may not be adjustable depending on the patient's bony anatomy.

When viewed from the top plan of FIG. 8, the angles 80, 82, and 84 defined between the arms 56 are also adjustable. The angles 80, 82, and 84 may be increased or decreased depending on the patient's bony anatomy to position the acetabular reamer guide 50 at the desired location and orientation. For example, any two of the arms 56 may be moved toward or away from each other. In other embodiments, the angles 80, 82, and 84 may or may not be adjustable depending on the patient's bony anatomy.

Figure 9:
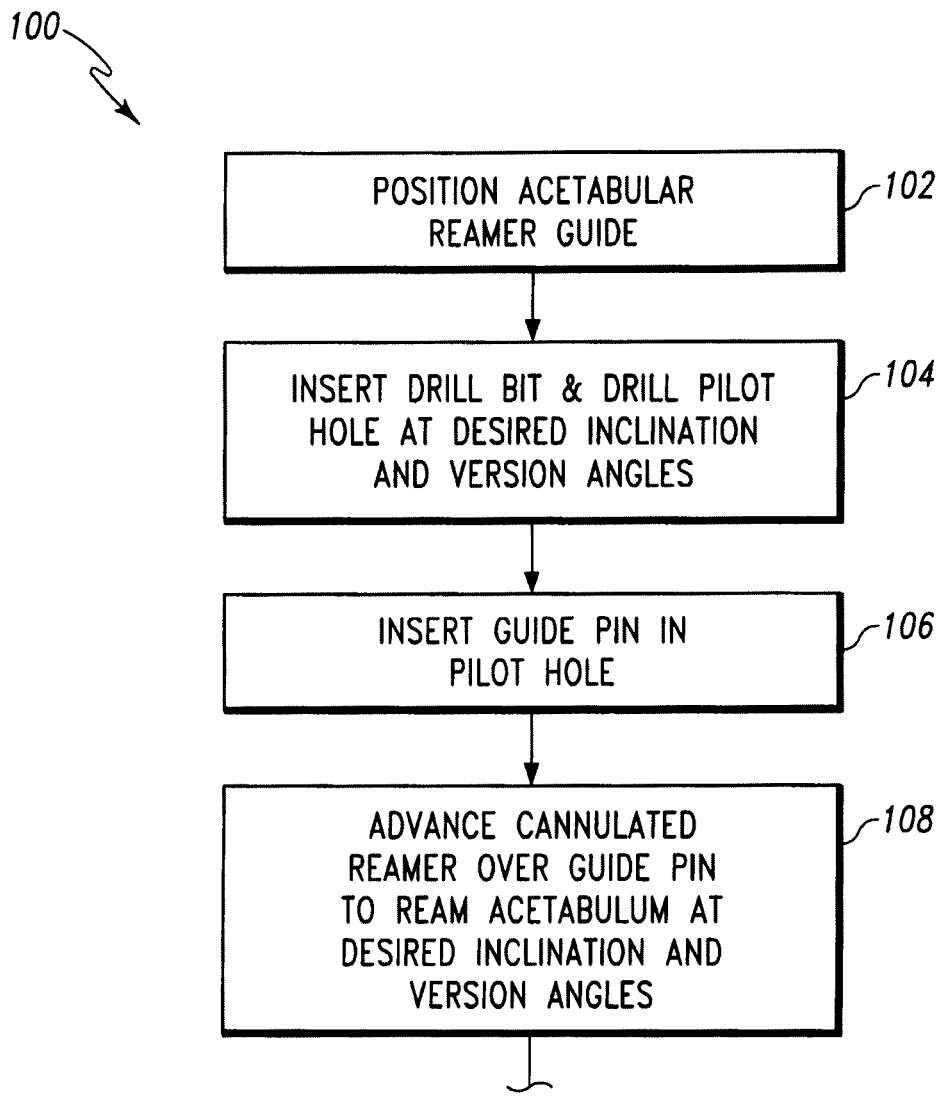
FIG. 9 is a simplified flow diagram of a method of performing an acetabular orthopaedic surgical procedure.

Referring to FIG. 9, an orthopaedic surgical procedure 100 using the acetabular reamer guide 50 is illustrated. The surgeon may perform the procedure 100 in process step 32 of method 10, which is illustrated in FIG. 1 and described above. In process step 102, the surgeon positions the acetabular reamer guide 50 on the patient's coxal bone. Because the acetabular reamer guide 50 is customized to the particular patient, the guide 50 is coupled to the patient's coxal bone in a substantially unique, predetermined location and orientation. For example, in those embodiments wherein the bottom surfaces 66 of the mounting feet 54 include a customized patient-specific contour, the acetabular reamer guide 50 is positioned on the patient's coxal bone such that a corresponding contour of the surface of the patient's coxal bone is received in the negative contour of the bottom surfaces 66 of the mounting feet 54. Additionally, in some embodiments, the surgeon may adjust the position of the acetabular reamer guide 50 pre-operatively or interoperatively. For example, in those embodiments wherein the each arm 56 is moveably secured to the drill guide 52 and each mounting foot 54, the surgeon may adjust the position of the acetabular reamer guide 50 to improve the coupling of the guide 50 to the patient's bony anatomy. Once positioned, the acetabular reamer guide 50 defines the desired inclination and version angles relative to the patient's acetabulum intended for the acetabular orthopaedic prosthesis.

In process step 104, the surgeon inserts a drill bit of an orthopaedic drill through the passageway 60 of the drill guide 52 of the acetabular reamer guide 50. The surgeon drills a pilot hole in the patient's acetabulum using the drill guide 52. It should be appreciated that the pilot hole is oriented to position the acetabular orthopaedic prosthesis at the desired inclination and version angles. Thereafter, the surgeon may remove the drill bit from the passageway 60.

In process step 106, the surgeon inserts a guide pin (see FIG. 10) through the passageway 60 of the drill guide 52 and into the pilot hole defined in the patient's acetabulum. The guide pin is then screwed or otherwise secured in the patient's acetabulum. After securing the guide pin to the patient's acetabulum, the surgeon removes the acetabular reamer guide 50, leaving the guide pin secured to the patient's acetabulum. Alternatively, in some embodiments, the surgeon may remove the acetabular reamer guide 50 after establishing the pilot hole in the patient's acetabulum. The surgeon may subsequently secure the guide pin in the pilot hole without the use of the drill guide 52.

Figure 10:
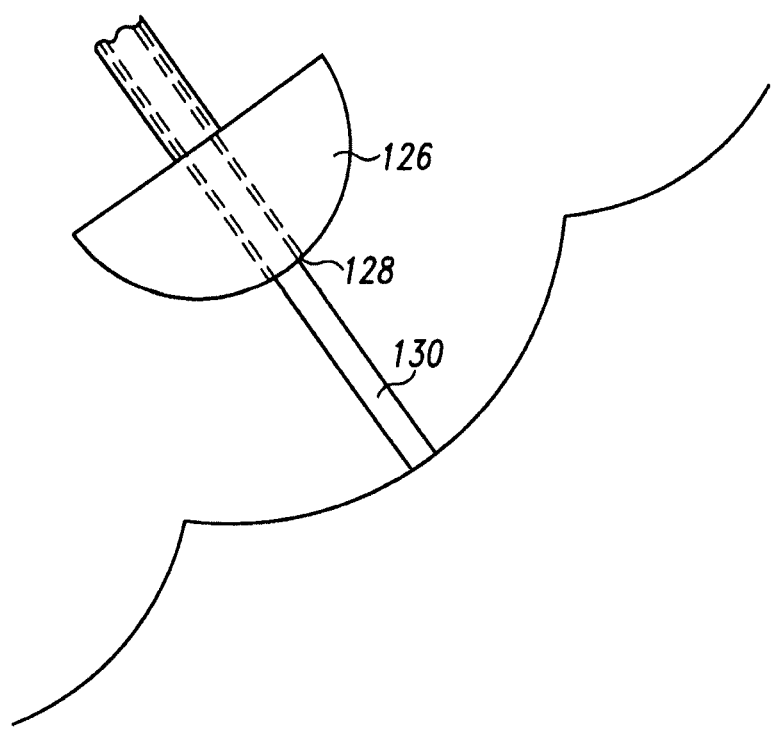
FIG. 10 is a perspective view of one embodiment of a cannulated reamer for use in the method of FIG. 9.

In process step 108, the surgeon advances a cannulated reamer (see FIG. 10) over the guide pin. As shown in FIG. 10, the cannulated reamer 126 includes a centrally-defined cannula or passageway 128 sized to receive a guide pin 130. The surgeon may advance the cannulated reamer 126 over the guide pin 130 to begin reaming the patient's acetabulum. It should be appreciated that because the guide pin 130 was secured to the patient's acetabulum in a predetermined location and orientation based on the desired version and inclination angle of the acetabular prosthesis, the reaming of the patient's acetabulum is guided so as to size the patient's acetabulum to receive the acetabular prosthesis according to the desired version and inclination angles.

Figure 11:
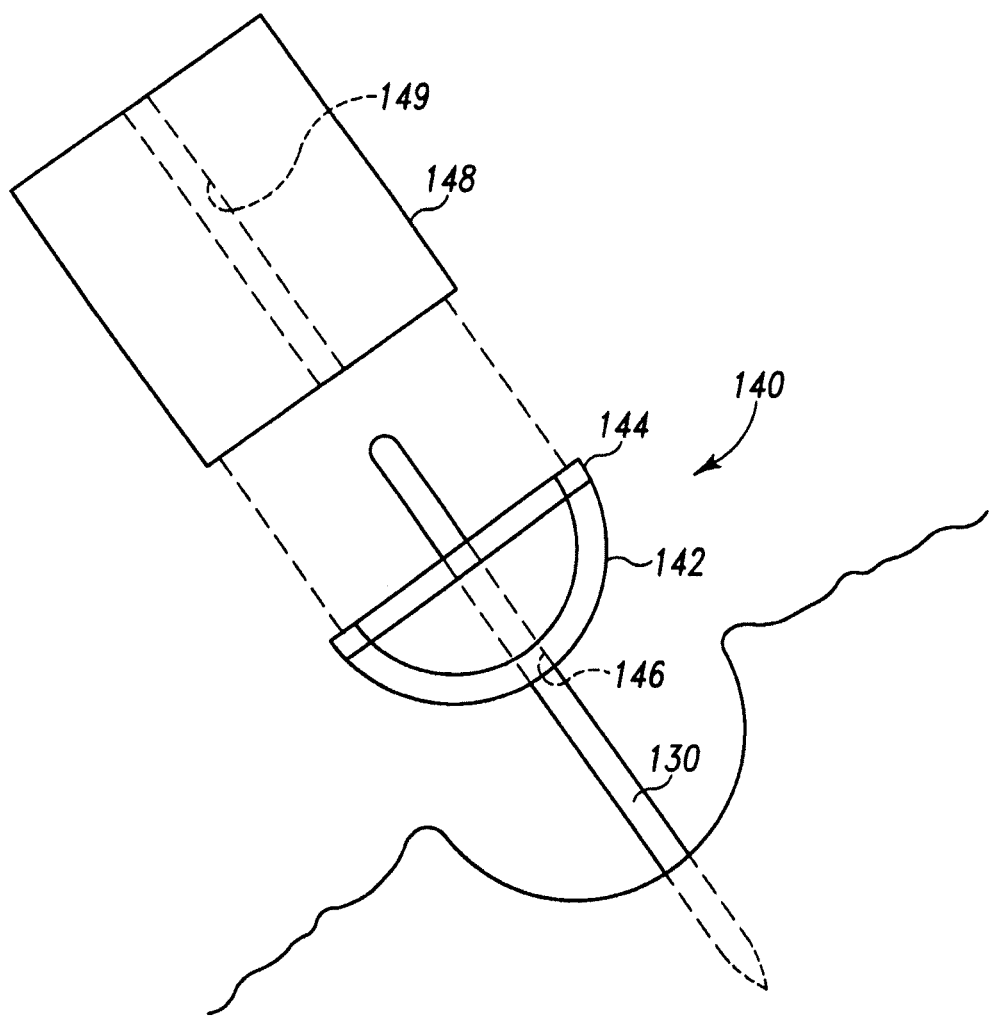
FIG. 11 is a side elevation view of an acetabular prosthesis positioned for implantation using a guide pin secured to the patient's bone via use of the customized patient-specific acetabular orthopaedic surgical instrument of FIG. 2 or FIG. 6.
Figure 12:
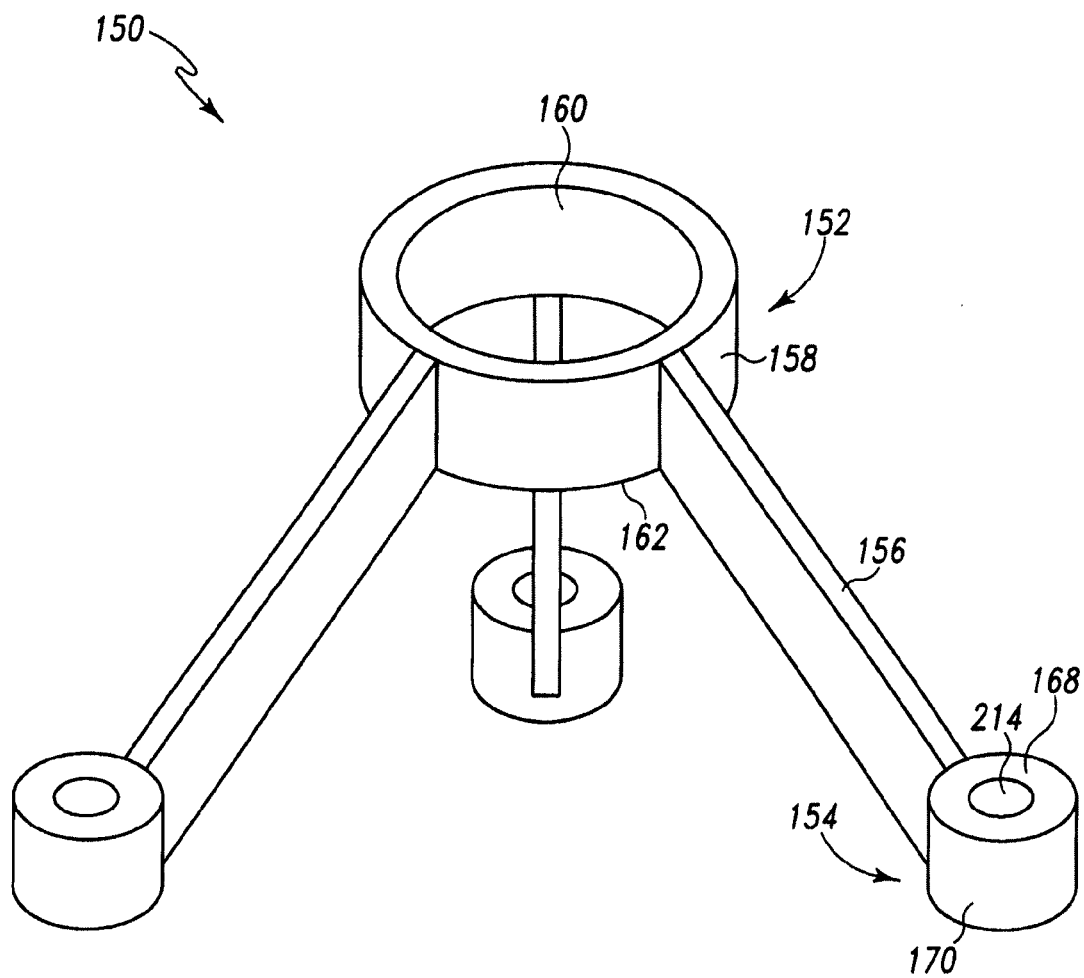
FIG. 12 is a perspective view of another embodiment of a customized patient-specific acetabular orthopaedic surgical instrument.

In some embodiments, the guide pin 130 may also be used as a guide during the implantation of an acetabular prosthesis. That is, as illustrated in FIG. 11, after the surgeon has reamed the patient's bone using the cannulated reamer 126, the surgeon may position an acetabular prosthesis 140, which may include an acetabular cup 142 and a bearing liner 144 received within the acetabular cup 142, over the guide pin 130. The acetabular prosthesis 140 includes an aperture 146, which may be threaded or non-threaded, positioned at the dwell point of the acetabular cup 142. The acetabular prosthesis 140 is positioned such that the guide pin 130 is received through the aperture 146. The acetabular prosthesis 140 may subsequently be slid down the guide pin 130 to the surgically-prepared acetabulum of the patient.

The acetabular prosthesis 140 may be implanted via use of an impactor or inserter 148. In the illustrative embodiment, the impactor 148 is substantially cylindrical in shape and has an outer diameter substantially equal to the outer diameter of the acetabular prosthesis 140. The impactor 148 is includes a centrally-positioned passageway 149, which is sized to receive the end of the guide pin 130 such that the impactor 148 may be positioned over the acetabular prosthesis 140. When so positioned, the impactor 148 contacts the rim of the acetabular prosthesis 140. The surgeon may then impact the impactor 148 (e.g., via use of a surgical hammer) to cause the acetabular prosthesis 140 to seed into the patient's surgically-prepared acetabulum. Of course, in other embodiments, other devices and tools may be used to implant the acetabular prosthesis 140 using the guide pin 130 as a guide. For example, in some embodiment, the impactor may be embodied as, or otherwise include, a stem configured to be received in the aperture 146. In such embodiments, the stem and aperture 146 are threaded. In addition, the stem is cannulated and configured to receive the guide pin 130 therein. In should be appreciated that in such embodiments, the aperture 146 has a greater diameter than the guide pin 130 to allow the stem of the impactor to be received therein. Regardless, once the acetabular prosthesis 140 is implanted, the guide pin 130 may be removed. It should be appreciated that because the acetabular prosthesis 140 is implanted using the guide pin 130 as a guide, the acetabular prosthesis 140 is implanted substantially at the predetermined location and orientation (e.g., at the predetermined inclination and version angles).

Although the acetabular reamer guide 50 has been described above in regard to a customized patient-specific instrument, it should be appreciated that the acetabular reamer guide 50 may not be customized to a specific patient in other embodiments. That is, in some embodiment the acetabular reamer guide 50 may be configured to use on a variety of patients. For example, the acetabular reamer guide 50 illustrated in FIG. 7 may be embodied as a non-patient-specific orthopaedic instrument. In such embodiments, the acetabular reamer guide 50 may be pre-operatively and/or intra-operatively adjusted by the surgeon to provide the desired inclination and version angles for the acetabular prosthesis. As such, it should be appreciated that because the acetabular reamer guide 50 is adjustable in such embodiments, the guide 50 may be used by the surgeon on a variety of patients and adjusted intra-operatively as desired by the orthopaedic surgeon.

Referring now to FIGS. 12-15, in another embodiment, the customized patient-specific acetabular orthopaedic surgical instrument may be embodied as an acetabular reamer guide 150. The acetabular reamer guide 150 is usable by a surgeon to secure multiple guide pins to the area of the patient's coxal bone proximate to the acetabulum in a predetermined location and orientation. The guide pins are subsequently used to orient and guide a cannulated reamer secured to the acetabular reamer guide 150 as discussed in more detail below.

The illustrative acetabular reamer guide 150 includes a reamer mount 152 and a plurality of mounting feet 154. Each of the mounting feet 154 is secured to the reamer mount 152 via a corresponding arm 156. In the illustrative embodiment of FIGS. 12-15, the arms 156, mounting feet 154, and reamer mount 152 are formed as a monolithic component from materials similar to those disclosed in regard to the embodiment of FIGS. 2-4. In other embodiments, the arms 156, mounting feet 154, and reamer mount 152 each may be formed as separate pieces and secured together by means similar to those disclosed in regard to the embodiment of FIGS. 2-4.

In the illustrative embodiment, the reamer mount 152 includes a body 158 having a reamer passageway 160 defined therethrough and a bottom surface 162. The illustrative body 158 has a substantially cylindrical shape but may have other shapes in other embodiments. The passageway 160 is sized such that a bone reamer 218 is insertable through the passageway 160 to secure the reamer 218 to the reamer mount 152, which is discussed in more detail below in regard to FIG. 15.

For example, the passageway 60 may have an inner diameter 64 (see FIG. 13) that is slightly larger than the outer diameter of the body 222 of the reamer 218. Additionally, the passageway 160 may have any cross-sectional shape suitable for receiving a cannulated reamer therethrough. For example, in FIGS. 12-15 the passageway 160 has a substantially circular cross-section, but in other embodiments, the body 158 may include a passageway 160 configured to receive a reamer 218 with a different cross-sectional shape.

Each of the mounting feet 154 is configured to contact the patient's bony anatomy during use. In the illustrative embodiment of FIGS. 12-15, each of the mounting feet 154 is substantially cylindrical in shape but may have other shapes in other embodiments, similar to those disclosed in regard to the embodiment of FIGS. 2-4. Each of the mounting feet 154 includes a bottom surface 166, which is configured to contact a portion of the patient's coxal bone proximate to the acetabulum. The mounting foot 154 also includes a top surface 168 opposite the bottom surface 166 and a sidewall 170. As discussed in greater detail below, the position of each mounting foot 154 relative to the reamer mount 152 and relative to each other allows the acetabular reamer guide 150 to be coupled to the patient's coxal bone in a substantially unique orientation and position. Additionally, in some embodiments, the bottom surface 166 of each mounting foot 154 may be customized to the contour of the patient's acetabulum. For example, similar to the embodiment illustrated in FIG. 5, the bottom surfaces 166 of the mounting feet 154 may be configured with a customized patient-specific negative contour configured to receive a portion of the corresponding contour of the patient's coxal bone proximate to the acetabulum. As such, the acetabular reamer guide 150 is configured to be coupled to the patient's coxal bone in a planned orientation and location, which has been predetermined to establish the desired inclination and version planes of the acetabular orthopaedic prosthesis.

Each mounting foot 154 includes drill guide passageway 214 defined therethrough. In the illustrative embodiment of FIG. 12, the passageways 214 are sized such that a guide pin is insertable through each passageway 214 to allow the guide pin to be secured to the patient's coxal bone proximate to the acetabulum. For example, the passageway 214 may have an inner diameter 216 that is slightly larger than the outer diameter of the guide pin. Additionally, the passageway 214 may have any cross-sectional shape suitable for receiving a drill bit of a bone drill and guide pin therethrough. For example, in FIGS. 12-15, the passageway 214 of each mounting foot 154 has a substantially circular cross-section, but in other embodiments, each mounting foot 154 may include a passageway 214 configured to receive a guide pin with a different cross-sectional shape.

Each of the mounting feet 154 has a length 174, which is based on the surface contour of the patient's bony anatomy such that the acetabular reamer guide 150 is positioned at the desired angles of inclination and version. For example, in the illustrative embodiment of FIG. 13, the length 174 of each mounting foot 154 is equal to one another. In other embodiments, the length 174 may be different relative to each mounting foot 154 to position the reamer guide 150 at the desired angles of inclination and version.

Figure 13:
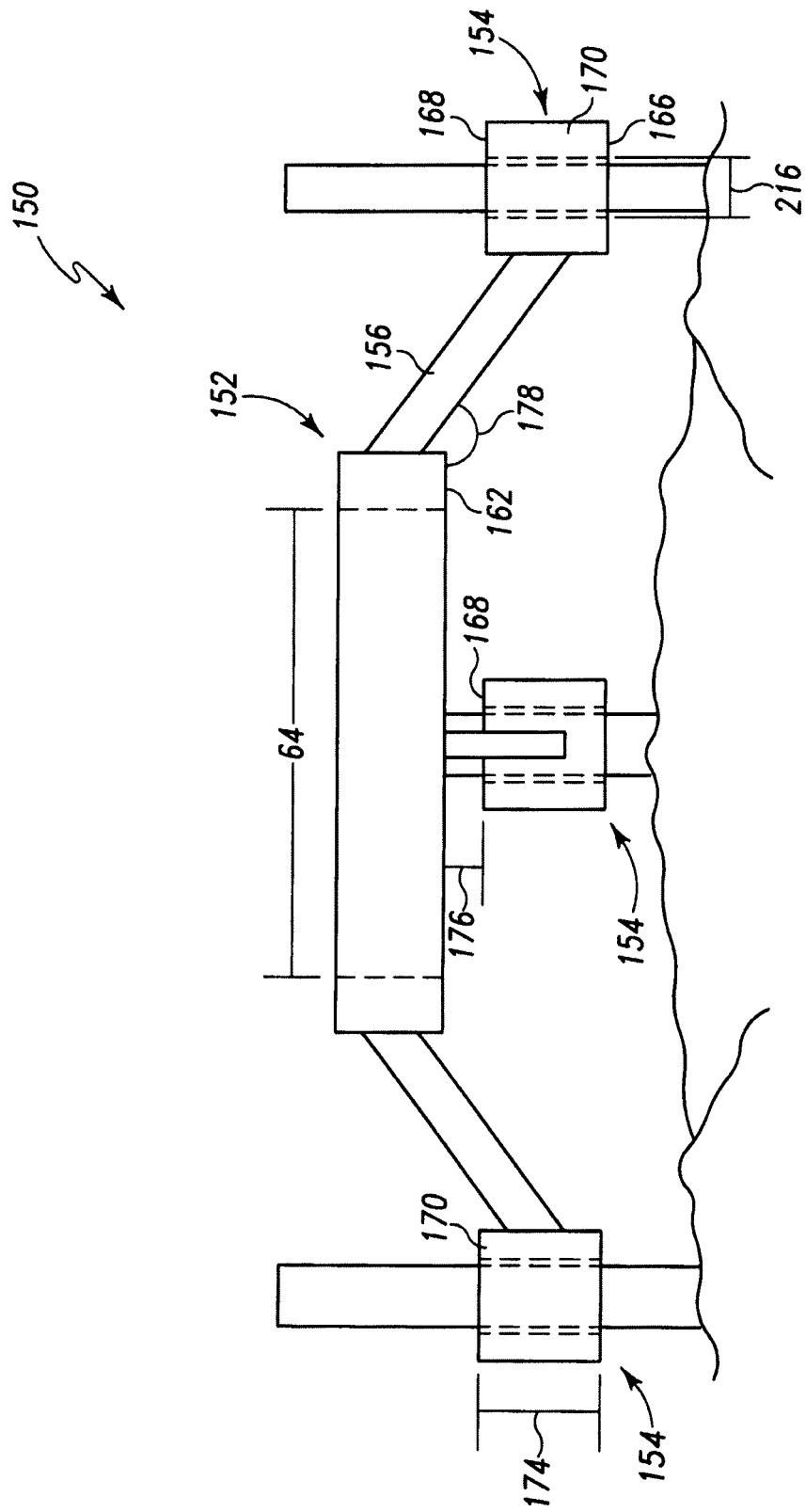
FIG. 13 is a side elevation view of the customized patient-specific acetabular orthopaedic surgical instrument of FIG. 12.

In some embodiments, as illustrated in FIG. 13, the bottom surface 162 of the reamer mount 152 may be offset a distance 176 from the top surface 168 of each mounting foot 154. In the illustrative embodiment of FIG. 12, the distance 176 for each mounting foot 154 is equal. In other embodiments, the distance 176 may be different such that the acetabular reamer guide 150 is positioned in the desired location and orientation, which has been predetermined to establish the desired inclination and version planes of the acetabular orthopaedic prosthesis. Additionally, in other embodiments, the bottom surface 162 of the reamer mount 152 may be coplanar with the top surface 168 of each mounting foot 154 such that the distance 176 is equal to zero. Further, in some embodiments, the reamer mount 152 may extend downwardly such that the bottom surface 162 of the reamer mount 152 is substantially equal to, higher than, or lower than the bottom surfaces 166 of the mounting feet 154.

As discussed above, the arms 156 secure the mounting feet 154 to the reamer mount 152. In the illustrative embodiment, the arms 156 are embodied as rectangular shafts, but may have other shapes and configurations in other embodiments, similar to those disclosed in regard to the embodiment of FIGS. 2-4. When viewed from the side elevation perspective of FIG. 13, an angle 178 is defined between each arm 156 and the bottom surface 162 of reamer mount 152. In the illustrative embodiment, each angle 178 is equal to one another. In other embodiments, each angle 178 may be different depending on the patient's anatomy and the desired angles of inclination and version of the acetabular orthopaedic prosthesis. Additionally, when viewed from the top plan of FIG. 14, each arm 156 extends a distance 186 from the reamer mount 152. It should be appreciated that in the illustrative embodiment of FIG. 14, the arms 156 extend the same distance 186 from the reamer mount 152. However, in other embodiments, each arm 156 may extend a distance 186 that is different from one another depending on the patient's anatomy and the desired angles of inclination and version of the acetabular orthopaedic prosthesis.

Figure 14:
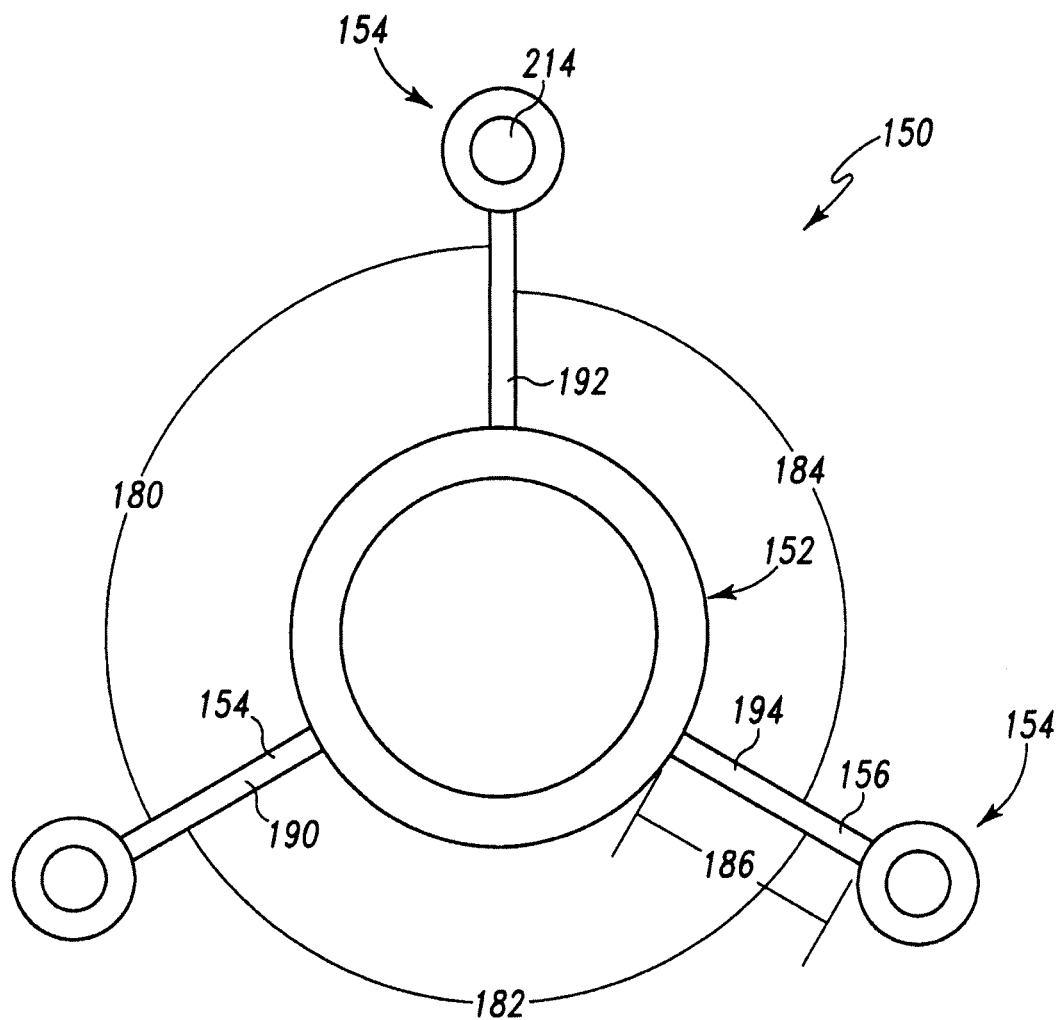
FIG. 14 is a top plan view of the customized patient-specific acetabular orthopaedic surgical instrument of FIG. 12.

Further, when viewed from the top plan of FIG. 14, the arms 156 extend from reamer mount 152 in a configuration so as to define a number of different angles 180, 182, and 184. For example, as illustrated in FIG. 14, an arm 190 and an arm 192 define an angle 180 therebetween, an arm 190 and an arm 194 define an angle 182 therebetween, and the arm 192 and the arm 194 define an angle 184 therebetween. In some embodiments, as shown in FIG. 14, the arms 156 extend from the reamer mount 152 in a substantially uniform configuration such that the angles 180, 182, and 184 are of substantially equal magnitude. Like many other dimensional characteristics described herein, the magnitude of the angles 180, 182, and 184 may be customized to any degree required for the particular patient. For example, in some embodiments, the magnitude of angle 184 may be greater than the magnitude of angle 182, which may be greater than the magnitude of angle 180.

Figure 15:
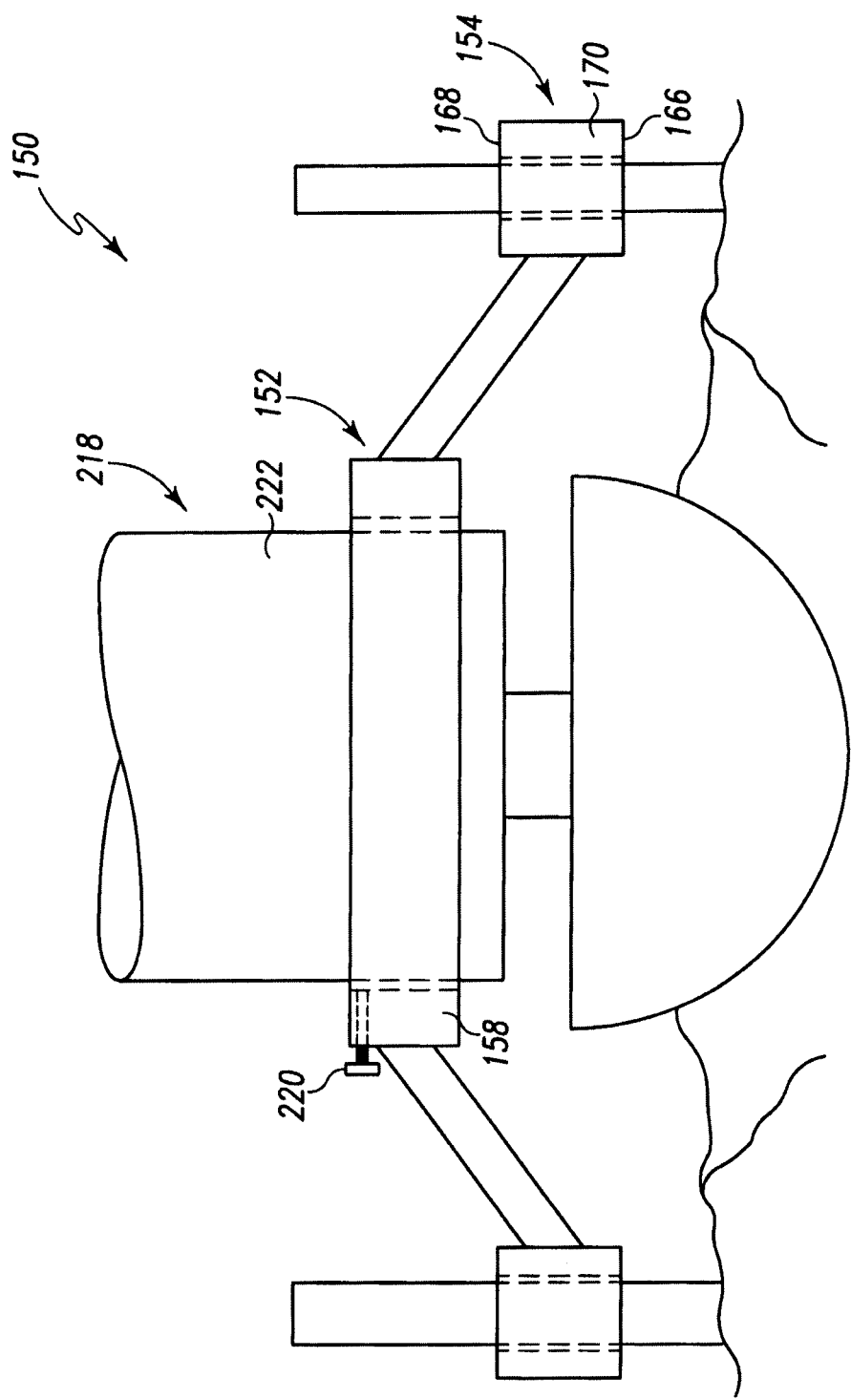
FIG. 15 is a side elevation view of the customized patient-specific acetabular orthopaedic of FIG. 12 coupled to a cannulated reamer.
Figure 16:
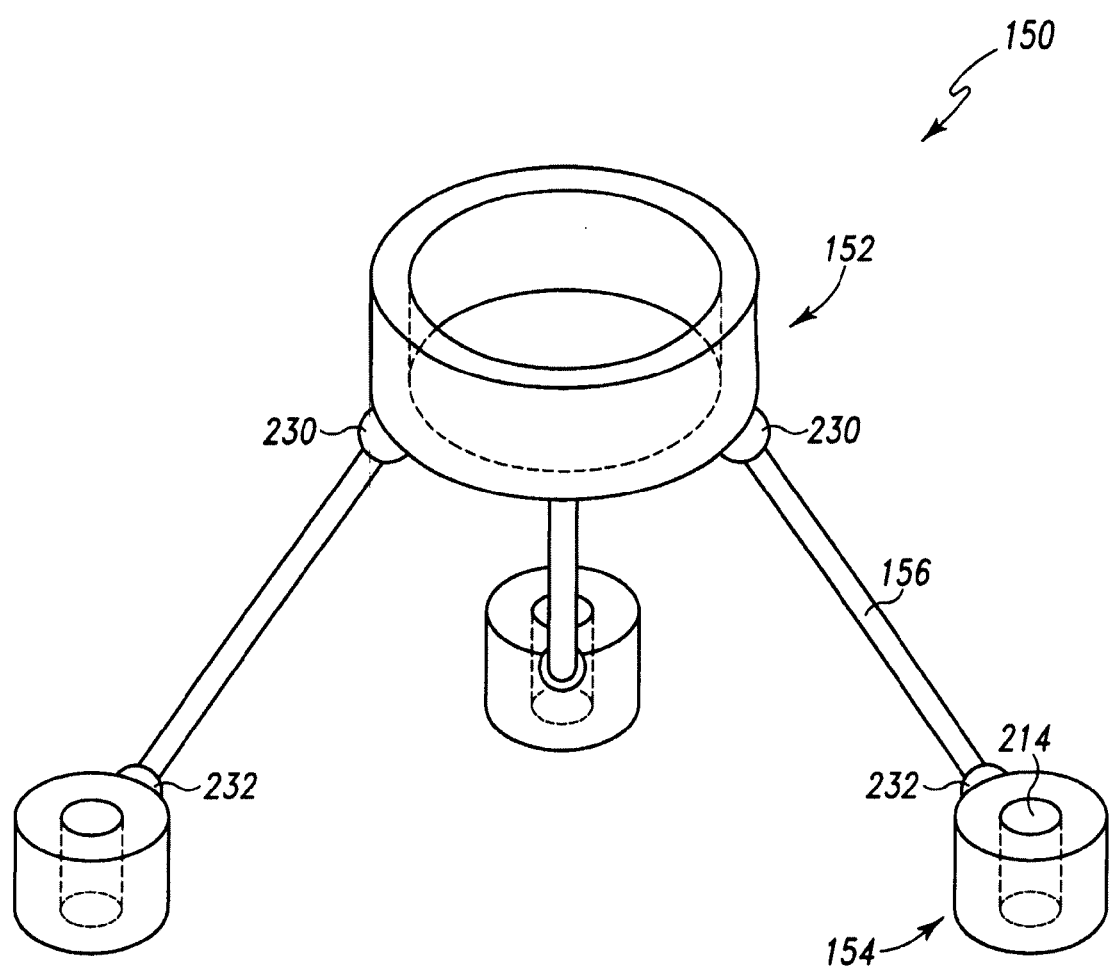
FIG. 16 is a perspective view of another embodiment of a customized patient-specific acetabular orthopaedic surgical instrument.
Figure 17:
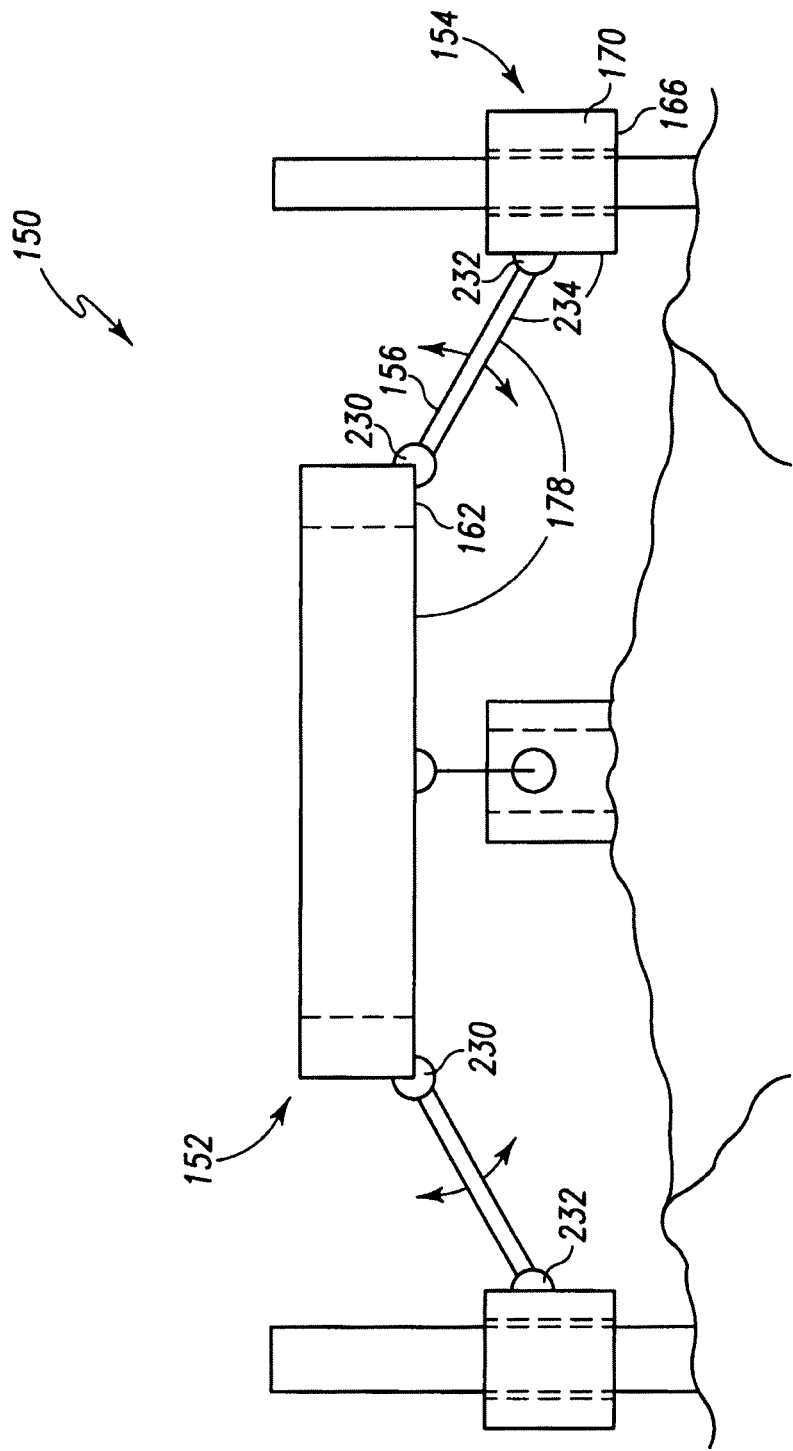
FIG. 17 is a side elevation view of the customized patient-specific acetabular orthopaedic surgical instrument of FIG. 16.

As illustrated in FIG. 15, the body 158 of the reamer mount 152 is secured to the reamer 218 such that the reamer 218 is oriented at the desired angles of inclination and version while reaming the patient's acetabulum. In the embodiment illustrated in FIG. 15, the reamer 218 is secured to the body 158 of the reamer mount 152 via a screw 220. It should be appreciated that the reamer 218 may be secured to the body 158 via other suitable fasteners such as bolts, adhesives, snapping tabs, or the like. Additionally, in other embodiments, the reamer 218 may or may not be secured to the body 158 of the reamer mount 152.

Referring now to FIGS. 16-19, in another embodiment, the acetabular reamer guide 150 is adjustable by the surgeon pre-operatively or interoperatively. Some features of the illustrative embodiment of FIGS. 16-19 are substantially similar to those discussed above in reference to the embodiment of FIGS. 12-15. Those features that are substantially similar have the same reference numbers as designated in the embodiment of FIGS. 12-15.

In the illustrative embodiment of FIGS. 16-19, each arm 156 is pivotally secured to the reamer mount 152 and each mounting foot 154. In particular, each arm 156 is secured to a joint 230 of reamer mount 152 and a corresponding joint 232 of each mounting foot 154. The joints 230, 232 may be embodied as hinges, universal joints, or the like configured to allow positioning of the mounting feet 154 relative to the drill guide 152. The joints 230, 232 may include a locking mechanism (not shown) capable of fixing each arm 156 at a desired position. It will be appreciated that in other embodiments not all arms 156 may be movably secured to the reamer mount 152 and/or mounting feet 154. Additionally, the acetabular reamer guide 150 may include any combination of joints to position the acetabular reamer guide 150 at the desired location and orientation to establish the desired inclination and version planes of the acetabular orthopaedic prosthesis.

It should be appreciated that the acetabular reamer guide 150 is adjustable by the orthopaedic surgeon to improve the coupling of the guide 150 to the patient's bony anatomy. For example, when viewed from the side elevation perspective of FIG. 17, each angle 178 defined between the bottom surface 162 of the reamer mount 152 and each arm 156 is adjustable to position the acetabular reamer guide 150 at the desired location and orientation. Additionally, an angle 234 is defined between each arm 156 and the sidewall 170 of each mounting foot 154. In the illustrative embodiment of FIG. 17, the angle 234 is adjustable to position the acetabular reamer guide 150 at the desired location and orientation. In other embodiments, each angle 234 may or may not be adjustable depending on the patient's bony anatomy.

Figure 18:
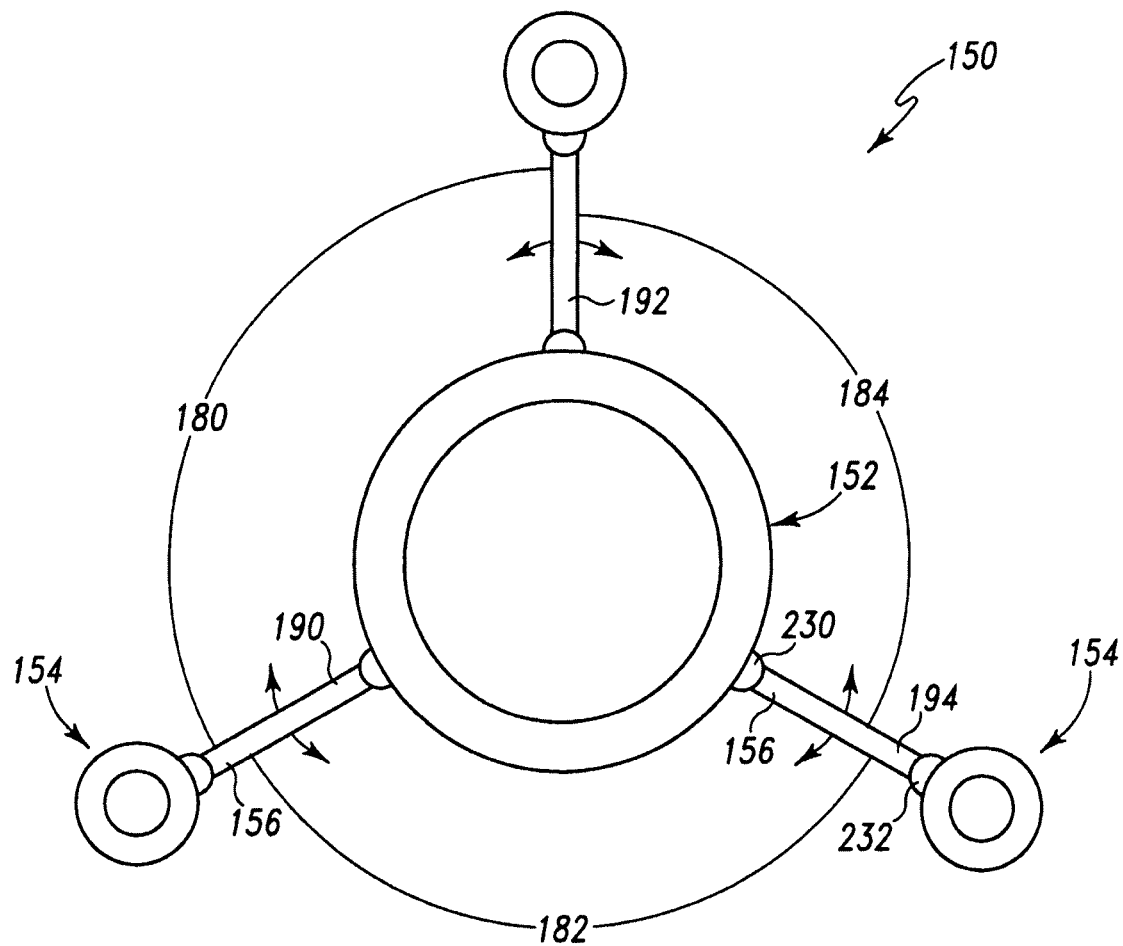
FIG. 18 is a top plan view of the customized patient-specific acetabular orthopaedic surgical instrument of FIG. 16.
Figure 19:
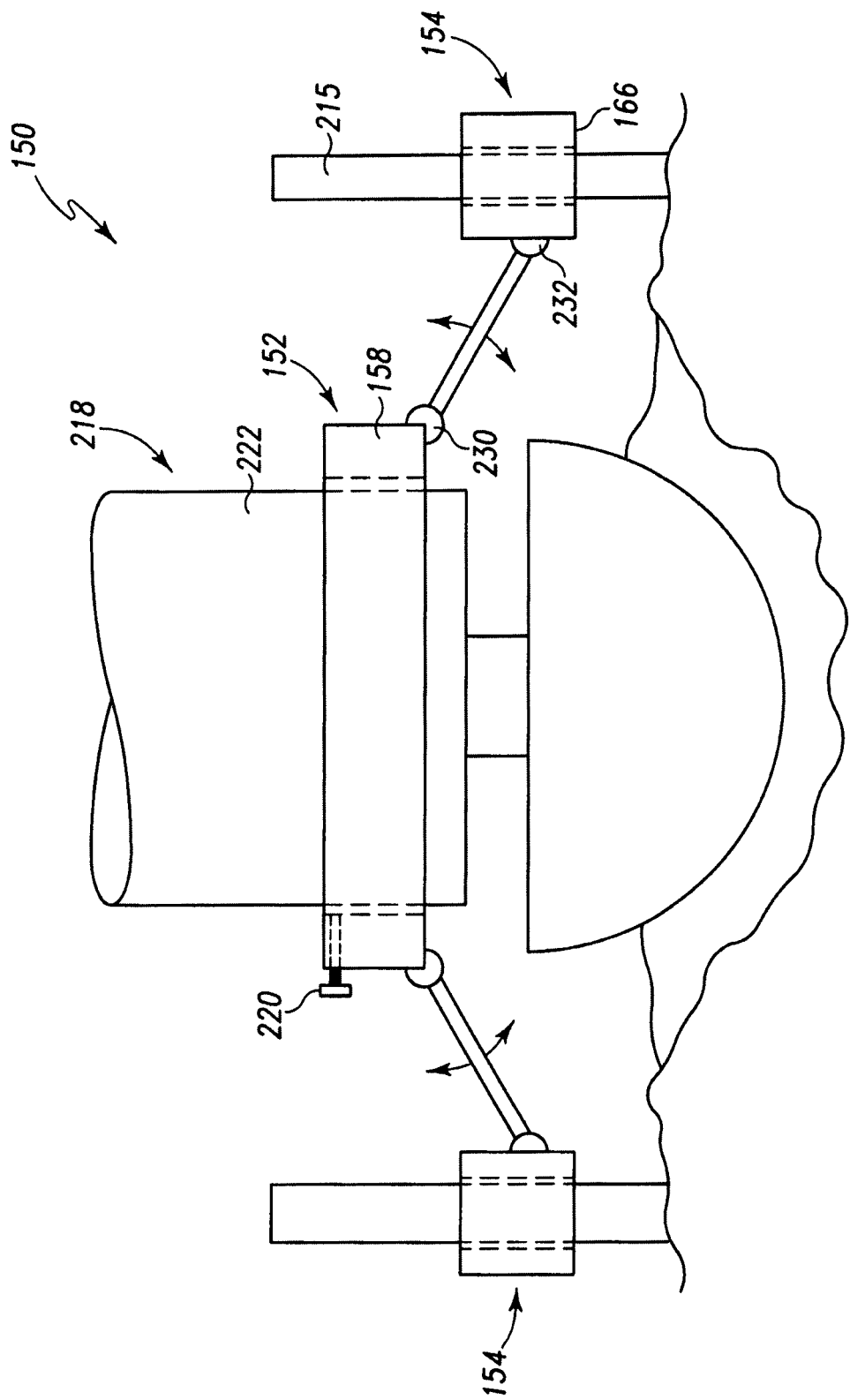
FIG. 19 is a side elevation view of the customized patient-specific acetabular orthopaedic surgical instrument of FIG. 16 coupled to an cannulated reamer.

When viewed from the top plan of FIG. 18, each angle 180, 182, and 184 defined between the arms 156 is also adjustable. The angles 180, 182, and 184 may be increased or decreased depending on the patient's bony anatomy to position the acetabular reamer guide 150 at the desired location and orientation. For example, any two of the arms 156 may be moved toward or away from each other. In other embodiments, the angles 180, 182, and 184 may or may not be adjustable depending on the patient's bony anatomy.

Figure 20:
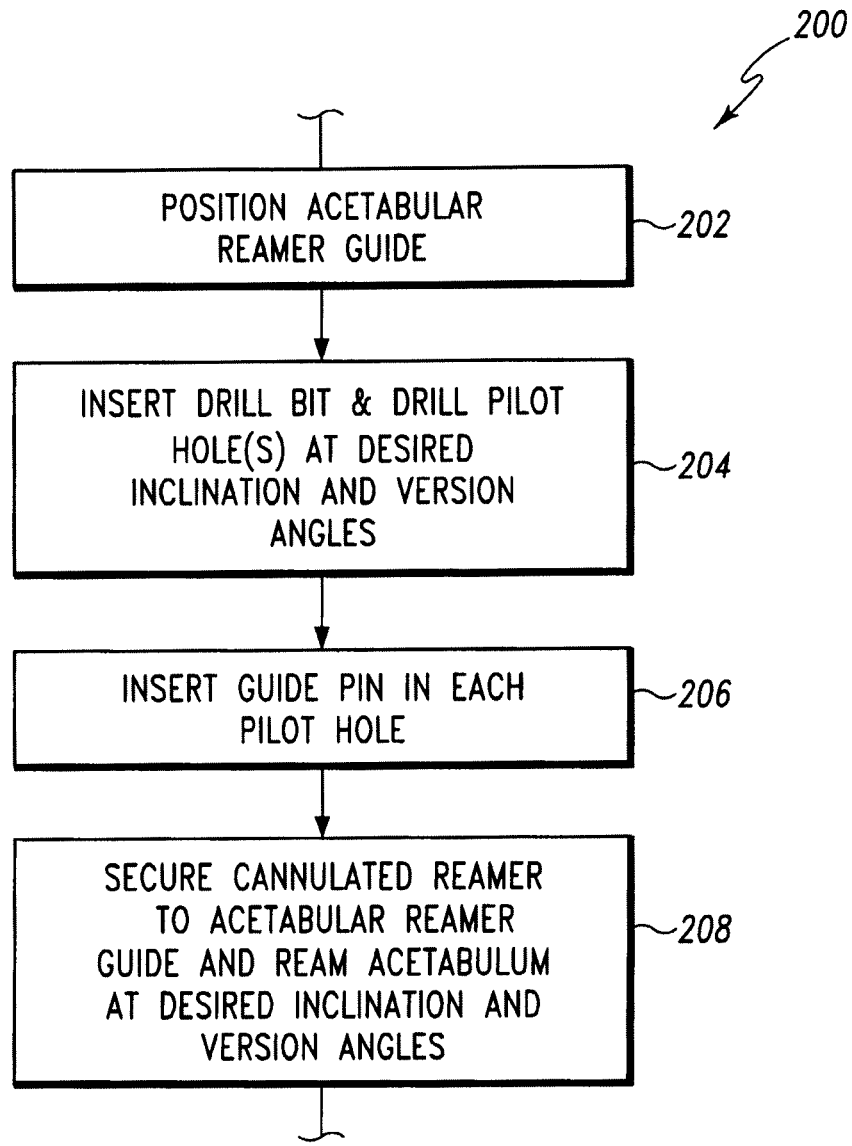
FIG. 20 is a simplified flow diagram of a method of performing an acetabular orthopaedic surgical procedure.

Referring to FIG. 20, an orthopaedic surgical procedure 200 using the acetabular reamer guide 150 is illustrated. The surgeon may perform the procedure 200 in process step 32 of method 10, which is illustrated in FIG. 1 and described above. In process step 202, the surgeon positions the acetabular reamer guide 150 on the patient's coxal bone. Because the acetabular reamer guide 50 is customized to the particular patient, the guide 150 is coupled to the patient's coxal bone in a substantially unique, predetermined location and orientation. For example, in those embodiments wherein the bottom surfaces 166 of the mounting feet 154 include a customized patient-specific contour, the acetabular reamer guide 150 is positioned on the patient's coxal bone such that a corresponding contour of the surface of the patient's coxal bone is received in the negative contour of the bottom surfaces 166 of the mounting feet 154. Additionally, in some embodiments, the surgeon may adjust the position of the acetabular reamer guide 150 pre-operatively or interoperatively. For example, in those embodiments wherein the each arm 156 is moveably secured to the reamer mount 152 and each mounting foot 154, the surgeon may adjust the position of the acetabular reamer guide 150 to improve the coupling of the guide 150 to the patient's bony anatomy. Once positioned, the acetabular reamer guide 150 defines the desired inclination and version angles relative to the patient's acetabulum intended for the acetabular orthopaedic prosthesis.

In process step 204, the surgeon inserts a drill bit of an orthopaedic drill through the passageway 214 of the first mounting foot 154 of the acetabular reamer guide 150. The surgeon drills a first pilot hole in the patient's coxal bone proximate to the acetabulum using the passageway 214 of the first mounting foot 154 as drilling guide. Thereafter, the surgeon may remove the drill bit from the passageway 214 of the first mounting foot 154. The surgeon repeats the process to drill a second and a third pilot hole in the patient's coxal bone proximate to the acetabulum using the passageway 214 of a second and third mounting foot 154. It should be appreciated that the first, second, and third pilot holes are oriented to position the acetabular orthopaedic prosthesis at the desired inclination and version angles.

In process step 206, the surgeon inserts a guide pin (see FIG. 15 or FIG. 19) through each passageway 214 of the mounting feet 154 and into the pilot hole defined in the patient's coxal bone proximate to the acetabulum. The guide pins are then screwed or otherwise secured in the patient's coxal bone. After securing the guide pins to the patient's acetabulum, the surgeon removes the acetabular reamer guide 150, leaving the guide pins secured to the patient's acetabulum. Alternatively, in some embodiments, the surgeon may remove the acetabular reamer guide 150 after establishing the pilot holes in the patient's acetabulum. The surgeon may subsequently secure the guide pins in the pilot holes without the use of the mounting feet 54.

In process step 208, the surgeon secures the bone reamer 218 to the acetabular reamer guide 150. The surgeon then advances the acetabular reamer guide 150 (see FIG. 15 or FIG. 19) over the guide pins to position the reamer 218 for reaming the patient's acetabulum. It should be appreciated that because the guide pins 215 were secured to the patient's acetabulum in a predetermined location and orientation based on the desired version and inclination angle of the acetabular prosthesis, the reaming of the patient's acetabulum is guided so as to size the patient's acetabulum to receive the acetabular prosthesis according to the desired version and inclination angles.

In some embodiments, the guide pins 215 may also be used as guides during the implantation of an acetabular prosthesis. That is, as illustrated in FIG. 21, after the surgeon has reamed the patient's bone using the bone reamer 218, the surgeon may secure an acetabular prosthesis 240, which may include an acetabular cup 242 and a bearing liner 244 received within the acetabular cup 242, to the acetabular reamer guide 150 via use of an impactor or inserter 248. The impactor 248 includes a housing or base 250 and a shaft 252 extending downwardly therefrom. The shaft 252 includes a threaded end 254, which is received in a threaded aperture 246 of the acetabular cup 242. The housing 250 of the impactor 248 is sized to be received in the reamer passageway 160 defined in the reamer mount 152 and secured to the mount 152 in a manner similar to the reamer 218 described in detail above.

Once the acetabular prosthesis 240 and impactor 248 have been secured to the acetabular reamer guide 150, the guide 150 is again slid over the guide pins 215, which provide a guide during implantation of the acetabular prosthesis. The acetabular reamer guide 150 may subsequently be slid down the guide pins 215 to the surgically-prepared acetabulum of the patient. The acetabular prosthesis 240 may subsequently be implanted via use of a impactor 248. To do so, the surgeon may impact the impactor 248 (e.g., via use of a surgical hammer) to cause the acetabular prosthesis 240 to seed into the patient's surgically-prepared acetabulum. Of course, in other embodiments, other devices and tools may be used to implant the acetabular prosthesis 240 using the guide pins 215 as guides. Regardless, once the acetabular prosthesis 140 is implanted, the guide pins 215 may be removed. It should be appreciated that because the acetabular prosthesis 240 is implanted using the guide pins 215 as a guides, the acetabular prosthesis 240 is implanted substantially at the predetermined location and orientation (e.g., at the predetermined inclination and version angles).

Although the acetabular reamer guide 150 has been described above in regard to a customized patient-specific instrument, it should be appreciated that the acetabular reamer guide 150 may not be customized to a specific patient in other embodiments. That is, in some embodiment the acetabular reamer guide 150 may be configured to use on a variety of patients. For example, the acetabular reamer guide 150 illustrated in FIG. 16 may be embodied as a non-patient-specific orthopaedic instrument. In such embodiments, the acetabular reamer guide 150 may be pre-operatively and/or intra-operatively adjusted by the surgeon to provide the desired inclination and version angles for the acetabular prosthesis. As such, it should be appreciated that because the acetabular reamer guide 150 is adjustable in such embodiments, the guide 150 may be used by the surgeon on a variety of patients and adjusted intra-operatively as desired by the orthopaedic surgeon.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A customized patient-specific orthopaedic instrument for facilitating implantation of an acetabular cup prosthesis in a coxal bone of a patient, the customized patient-specific orthopaedic instrument comprising:

a customized patient-specific acetabular reaming guide comprising a single monolithic component including (i) a body having a longitudinal passageway defined therethrough, (ii) a plurality of arms extending from the body, and (iii) a plurality of feet configured to contact a coxal bone of a patient, each foot of the plurality of feet being coupled to a corresponding arm of the plurality of arms, an acetabular reamer surgical tool configured to ream the patient's acetabulum, the acetabular reamer surgical tool including a body positioned in the longitudinal passageway of the customized patient-specific acetabular reaming guide and secured thereto, wherein (i) each foot of the plurality of feet is non-movably fixed relative to the body based on (i) a predetermined degrees of version and inclination angles of the acetabular cup prosthesis when implanted in the patient's coxal bone, (ii) each foot of the plurality of feet includes a longitudinal passageway defined therein that is sized to receive a bone guide pin, and (iii) each foot of the plurality of feet includes a bottom, bone-facing surface having a customized patient-specific negative contour configured to receive a portion of the patient's coxal bone surrounding the patient's acetabulum having a corresponding positive contour, the customized patient-specific negative contour of each foot being unique relative to the customized patient-specific negative contour of every other foot to orient the acetabular reamer surgical tool at the predetermined degree of version and inclination angles when the customized patient-specific acetabular reaming guide is engaged with the patient's coxal bone.

2. The customized patient-specific orthopaedic instrument of claim 1, wherein:
the body includes a bottom, bone-facing surface and each foot of the plurality of feet includes a top surface,
the bottom, bone-facing surface of the body being non-coplanar with respect to a plane defined by the top surface of at least one of the plurality of feet.

3. The customized patient-specific orthopaedic instrument of claim 1, wherein:
the body includes a bottom, bone-facing surface and each foot of the plurality of feet includes a top surface,
the bottom, bone-facing surface of the body and each top surface of the plurality of feet being coplanar with respect to each other.

4. The customized patient-specific orthopaedic instrument of claim 1, wherein:
the body includes a bottom, bone-facing surface and the plurality of feet includes a first foot having a first top surface defining a first plane and a second foot having a second top surface defining a second plane,
the bottom, bone-facing surface of the body, the first top surface, and the second top surface are parallel and non-coplanar with respect to each other.

5. The customized patient-specific orthopaedic instrument of claim 1, wherein:
the body includes a bottom, bone-facing surface and each foot of the plurality of feet includes a bottom surface,
the bottom, bone-facing surface of the body being positioned medially with respect to the bottom surface of each foot of the plurality of feet when the customized patient-specific acetabular reaming guide is positioned in contact with the patient's coxal bone.

6. The customized patient-specific orthopaedic instrument of claim 1, wherein each foot of the plurality of feet has a longitudinal length different from each other.

7. The customized patient-specific orthopaedic instrument of claim 1, wherein the body includes a sidewall and each arm of the plurality of arms includes a bottom surface,
wherein each bottom surface of the plurality of arms define an angle with respect to the sidewall of the body that is different in magnitude with respect to the angle defined by each other bottom surface of the plurality of arms.

8. The customized patient-specific orthopaedic instrument of claim 1, wherein an angle is defined between each arm of the plurality of arms with respect to another adjacent arm of the plurality of arms when viewed in a top plan view, each of the angles being different in magnitude from each other.

9. The customized patient-specific orthopaedic instrument of claim 1, wherein a distance is defined between each foot of the plurality of feet and the body when viewed in a top plan view, and each distance is different in magnitude than each of the other distances defined between the body and each other foot of the plurality of feet.

10. The customized patient-specific orthopaedic instrument of claim 1, wherein the plurality of arms comprises at least three arms extending from the body.

* * * * *